(12) United States Patent
Klein

(10) Patent No.: US 9,006,255 B2
(45) Date of Patent: Apr. 14, 2015

(54) QUINAZOLINE DERIVATIVES

(75) Inventor: Markus Klein, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 42 days.

(21) Appl. No.: 13/881,531

(22) PCT Filed: Sep. 22, 2011

(86) PCT No.: PCT/EP2011/004745
§ 371 (c)(1),
(2), (4) Date: Apr. 25, 2013

(87) PCT Pub. No.: WO2012/055466
PCT Pub. Date: May 3, 2012

(65) Prior Publication Data
US 2013/0210819 A1    Aug. 15, 2013

(30) Foreign Application Priority Data

Oct. 26, 2010    (DE) .......................... 10 2010 049 595

(51) Int. Cl.
*A61K 31/517*    (2006.01)
*C07D 471/04*    (2006.01)
*A61K 31/519*    (2006.01)
*A61K 31/538*    (2006.01)
*A61K 45/06*    (2006.01)

(52) U.S. Cl.
CPC ............ *C07D 471/04* (2013.01); *A61K 31/517* (2013.01); *A61K 31/519* (2013.01); *A61K 31/538* (2013.01); *A61K 45/06* (2013.01)

(58) Field of Classification Search
CPC ............................. C07D 471/04; A61K 31/517
USPC .................. 544/279, 284; 514/230.5, 264.11, 514/266.21, 264.1
See application file for complete search history.

(56) References Cited

U.S. PATENT DOCUMENTS

2009/0018131 A1    1/2009  Adams et al.
2010/0179144 A1    7/2010  Adams et al.

FOREIGN PATENT DOCUMENTS

WO    2008/157191 A2    12/2008

OTHER PUBLICATIONS

Finan, Peter. "PI3-Kinase Inhibition: A Target for Therapeutic Intervention" Protein Tyrosine Kinases. Dorano Fabbro. (2006) Humana Press. 53-69.*
MedlinePlus: Autoimmune Diseases. Jul. 21, 2014. <http://www.nlm.nih.gov/medlineplus/autoimmunediseases.html>.*
What is Cardiovascular Disease? (2011). <http://www.heart.org/HEARTORG/Caregiver/Resources/WhatisCardiovascularDisease/What-is-Cardiovascular-Disease_UCM_301852_Article.jsp.>.*
Degenerative Nerve Diseases. (2014). <http://www.nlm.nih.gov/medlineplus/degenerativenervediseases.html>.*
Multiple organ failure. (2012) <medterms.com>.*
MedlinePlus. Kidney diseases. (2014) <http://www.nlm.nih.gov/medlineplus/kidneydiseases.html>.*
Definition of Cancer. (2004) <www.medterms.com>)\.*
WebMD. Lung Injuries. (2012) <http://www.webmd.com/lung/lung-injuries>.*
International Search Report for PCT/EP2011/004745 (Nov. 9, 2011).

* cited by examiner

*Primary Examiner* — Golam M M Shameem
*Assistant Examiner* — Laura Daniel
(74) *Attorney, Agent, or Firm* — Millen, White, Zelano & Branigan, P.C.

(57) ABSTRACT

Compounds of the formula I in which R, X, $L^2$ and $A^1$-$A^6$ have the meanings indicated in Claim 1, are PI3K inhibitors and can be employed, inter alia, for the treatment of autoimmune diseases, inflammation, cardiovascular diseases, neurodegenerative diseases and tumors.

15 Claims, No Drawings

QUINAZOLINE DERIVATIVES

BACKGROUND OF THE INVENTION

The invention was based on the object of finding novel compounds having valuable properties, in particular those which can be used for the preparation of medicaments.

The present invention relates to compounds and the use thereof for the modulation, in particular for the inhibition, of the activity or function of the phosphoinositide 3'-OH kinase family (hereinafter PI3 kinases), advantageously PI3Kα, PI3Kδ, PI3Kβ and/or PI3Kγ. The present invention advantageously relates to the use of quinoxaline derivatives in the treatment of one or more disease states selected from: autoimmune disorders, inflammatory diseases, cardiovascular diseases, neurodegenerative diseases, allergy, asthma, pancreatitis, multiorgan failure, kidney diseases, blood platelet aggregation, cancer, sperm motility, transplant rejection, graft rejection and lung injuries.

Cell membranes provide a large store of secondary messengers that can be enlisted in a variety of signal transduction pathways. As regards the function and regulation of effector enzymes in phospholipid signalling pathways, these enzymes generate secondary messengers from the membrane phospholipid pools. Class I PI3 kinases (for example PI3Kα) are dual-specificity kinase enzymes, i.e. they exhibit both lipid kinase activity (phosphorylation of phosphoinositides) and protein kinase activity, shown to be capable of phosphorylation of protein as substrate, including autophosphorylation as intramolecular regulatory mechanism. These enzymes of phospholipid signalling are activated by various extracellular signals, such as growth factors, mitogens, integrins (cell-cell interactions), hormones, cytokines, viruses, and neurotransmitters, as described in Scheme I below, and also by intracellular regulation by other signaling molecules (cross-talk, where the original signal can activate some parallel pathways, which in a second step transmit signals to PI3Ks by intracellular signaling events), such as, for example, small GTPases, kinases, or phosphatases. Intracellular regulation can also occur as a result of aberrant expression or lack of expression of cellular oncogenes or tumour suppressors. The intracellular inositol phopholipid (phosphoinositide) signaling pathways begin with activation of signaling molecules (extracellular ligands, stimuli, receptor dimerisation, transactivation by a heterologous receptor (for example receptor tyrosine kinase) and with the recruitment and activation of PI3K, including the involvement of G protein-linked trans-membrane receptor integrated into the plasma membrane.

PI3K converts the membrane phospholipid PI(4,5)P$_2$ into PI(3,4,5)P$_3$, which functions as secondary messenger. PI and PI(4)P are likewise substrates of PI3K and can be phosphorylated and converted into PI3P and PI(3,4)P$_2$, respectively. In addition, these phosphoinositides can be converted into other phosphoinositides by 5'-specific and 3'-specific phosphatases, meaning that PI3K enzyme activity results either directly or indirectly in the generation of two 3'-phosphoinositide subtypes which function as secondary messengers in intracellular signal transduction pathways (Trends Biochem. Sci. 22(7) pp. 267-72 (1997) by Vanhaesebroeck et al; Chem. Rev. 101(8) pp. 2365-80 (2001) by Leslie et al (2001); Annu. Rev. Cell. Dev. Biol. 17p, 615-75 (2001) by Katso et al. and Cell. Mol. Life Sci. 59(5) pp. 761-79 (2002) by Toker et al.). Multiple PI3K isoforms categorised by their catalytic subunits, their regulation by corresponding regulatory subunits, expression patterns and signal-specific functions (p110α, β, δ and γ) perform this enzyme reaction (Exp. Cell. Res. 25 (1) pp. 239-54 (1999) by Vanhaesebroeck and Katso et al., 2001, see above).

The closely related isoforms p110α and β are expressed ubiquitously, while δ and γ are expressed more specifically in the haematopoietic cell system, in the smooth muscle cells, myocytes and endothelial cells (Trends Biochem. Sci. 22(7) pp. 267-72 (1997) by Vanhaesebroeck et al.). Their expression can also be regulated in an inducible manner depending on the cellular tissue type and stimuli as well as in accordance with the particular disease. The inducibility of protein expression includes protein synthesis as well as protein stabilisation, which is partly regulated by association with regulatory subunits.

To date, eight mammalian PI3Ks have been identified, divided into 3 main classes (I, II and III) on the basis of sequence homology, structure, binding partners, mode of activation, and substrate preference. In vitro, class I PI3Ks are able to phosphorylate phosphatidylinositol (PI), phosphatidylinositol 4-phosphate (PI4P) and phosphatidylinositol 4,5-bisphosphate (PI(4,5)P$_2$) to give phosphatidylinositol 3-phosphate (PI3P), phosphatidylinositol 3,4-bisphosphate (PI(3,4)P$_2$, and phosphatidylinositol 3,4,5-trisphosphate (PI (3,4,5)P$_3$, respectively. Class II PI3Ks phosphorylate PI and phosphatidylinositol 4-phosphate. Class III PI3Ks can only phosphorylate PI (Vanhaesebroeck et al., 1997, see above; Vanhaesebroeck et al., 1999, see above, and Leslie et al, 2001, see above).

Scheme I: Conversion of PI(4,5)P2 into PIP3

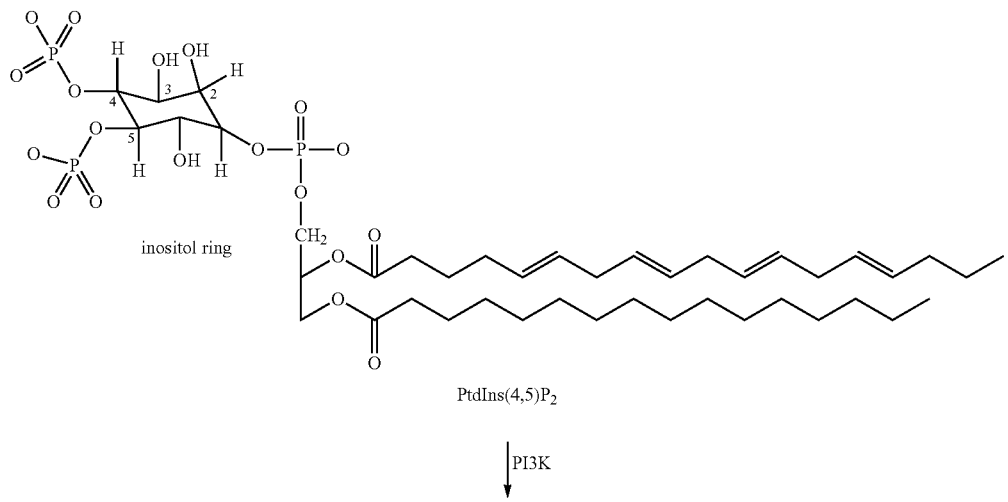

PtdIns(4,5)P$_2$

↓ PI3K

-continued

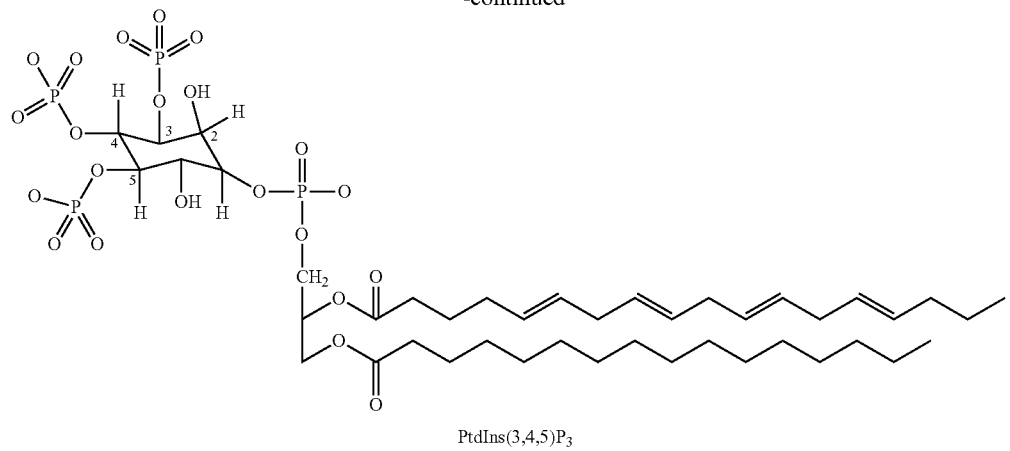

PtdIns(3,4,5)P$_3$

As illustrated in Scheme I above, phosphoinositide 3-kinases (PI3Ks) phosphorylate the hydroxyl of the third carbon atom on the inositol ring. The phosphorylation of phosphoinositides which converts PtdIns into 3,4,5-triphosphate (PtdIns(3,4,5)P$_3$), PtdIns(3,4)P$_2$ and PtdIns(3)P produces secondary messengers for various signal transduction pathways, as are essential, inter alia, for cell proliferation, cell differentiation, cell growth, cell size, cell survival, apoptosis, adhesion, cell mobility, cell migration, chemotaxis, invasion, cytoskeletal rearrangement, cell shape changes, vesicle trafficking and metabolic pathway (Katso et al, 2001, see above, and Mol. Med. Today 6(9) pp. 347-57 (2000) by Stein). G protein-coupled receptors mediate phosphoinositide 3'-OH kinase activation via small GTPases, such as Gβγ and Ras, and consequently PI3K signaling plays a central role in the development and coordination of cell polarity and dynamic organisation of the cytoskeleton—which together provide the driving force for cell movement.

Chemotaxis—the directed movement of cells in the direction of a concentration gradient of chemical attractants, which are also called chemokines, is also involved in many important diseases, such as inflammation/autoimmunity, neurodegeneration, angiogenesis, invasion/metastasis and wound healing (Immunol. Today 21(6) pp. 260-4 (2000) by Wyman et al.; Science 287(5455) pp. 1049-53 (2000) by Hirsch et al.; FASEB J. 15(11) pp. 2019-21 (2001) by Hirsch et al., and Nat. Immunol. 2(2) pp. 108-15 (2001) by Gerard et al.).

Advances using genetic approaches and pharmacological tools have provided insights into signalling and molecular pathways which promote chemotaxis in response to chemical attractant-activated, G protein-coupled sensors. PI3 kinase, which is responsible for the generation of these phosphorylated signalling products, was originally identified as an activity which is associated with viral oncoproteins and growth factor tyrosine kinases which phosphorylate phosphatidylinositol (PI) and its phosphorylated derivatives at the 3'-hydroxyl of the inositol ring (Panayotou et al., Trends Cell Biol. 2 pp. 358-60 (1992)). However, more recent biochemical studies have shown that class I PI3 kinases (for example class IB isoform PI3Kγ) are dual-specificity kinase enzymes, which means that they exhibit both lipid kinase activity and protein kinase activity, shown to be capable of phosphorylation of other proteins as substrates, as well as autophosphorylation as an intramolecular regulatory mechanism.

PI3 kinase activation is therefore probably involved in various cellular responses, including cell growth, differentiation and apoptosis (Parker et al., Current Biology, 5 pp. 577-99 (1995); Yao et al., Science, 267 pp. 2003-05 (1995)). PI3 kinases appear to be involved in a number of aspects of leukocyte activation. A p85-associated PI3 kinase activity has been shown to associate physically with the cytoplasmic domain of CD28, which is an important co-stimulatory molecule for the activation of T cells by antigen (Pages et al., Nature, 369 pp. 327-29 (1994); Rudd, Immunity 4 pp. 527-34 (1996)). Activation of T cells by CD28 lowers the threshold for activation by antigen and increases the magnitude and duration of the proliferative response. These effects are accompanied by increases in the transcription of a number of genes, such as, inter alia, interleukin-2 (IL2), an important T cell growth factor (Fraser et al., Science 251 pp. 313-16 (1991)). If CD28 is mutated in such a way that it can no longer interact with PI3 kinase, initiation of IL-2 production fails, which suggests a crucial role for PI3 kinase in T cell activation. PI3Kγ has been identified as a promoter of G-β-γ-dependent regulation of JNK activity, and G-β-γ are subunits of heterotrimeric G proteins (Lopez-Ilasaca et al, J. Biol. Chem. 273(5) pp. 2505-8 (1998)). Cellular processes in which PI3Ks play an essential role include suppression of apoptosis, reorganisation of the actin skeleton, cardiac myocyte growth, glycogen synthase stimulation by insulin, TNFα-promoted neutrophil priming and superoxide generation, and leukocyte migration and adhesion to endothelial cells.

Laffargue et al., Immunity 16(3) pp. 441-51 (2002), have described that PI3Kγ relays inflammatory signals via various G(i)-coupled receptors and that it is crucial for mast cell function, stimuli in connection with leukocytes, and immunology, including cytokines, chemokines, adenosines, antibodies, integrins, aggregation factors, growth factors, viruses or hormones (J. Cell. Sci. 114(Pt 16) pp. 2903-10 (2001) by Lawlor et al.; Laffargue et al., 2002, see above, and Curr. Opinion Cell Biol. 14(2) pp. 203-13 (2002) by Stephens et al.).

Specific inhibitors against individual members of a family of enzymes provide invaluable tools for deciphering the functions of each enzyme. Two compounds, LY294002 and wortmannin (see below), have been widely used as PI3 kinase inhibitors. These compounds are non-specific PI3K inhibitors, since they do not distinguish between the four members of class I PI3 kinases. For example, the IC$_{50}$ values of wortmannin against each of the various class I PI3 kinases are in the range from 1 to 10 nM. Correspondingly, the IC$_{50}$ values of LY294002 against each of these PI3 kinases are about 15 to 20 μM (Fruman et al., Ann. Rev. Biochem., 67, pp. 481-507 (1998)), in addition it has $IC_{50}$ values of 5-10 μM on CK2 protein kinase and a slight inhibitory activity on phospholipases. Wortmannin is a fungal metabolite which irreversibly inhibits PI3K activity by bonding covalently to the catalytic domain of this enzyme. The inhibition of PI3K activity by wortmanin eliminates the subsequent cellular response to the extracellular factor. For example, neutrophils respond to the chemokine fMet-Leu-Phe (fMLP) by stimulation of PI3K and synthesis of PtdIns $(3,4,5)P_3$. This synthesis correlates with activation of the respiratory burst which is involved in the destruction of the neutrophils of invading microorganisms. Treatment of neutrophils with wortmannin prevents the fMLP-induced respiratory burst response (Thelen et al., Proc. Natl. Acad. Sci. USA, 91, pp. 4960-64 (1994)). Indeed, these experiments with wortmannin, as well as other experimental evidence, show that PI3K activity in cells of haematopoietic lineage, in particular neutrophils, monocytes and other types of leukocytes, are involved in many of the non-memory immune response associated with acute and chronic inflammation.

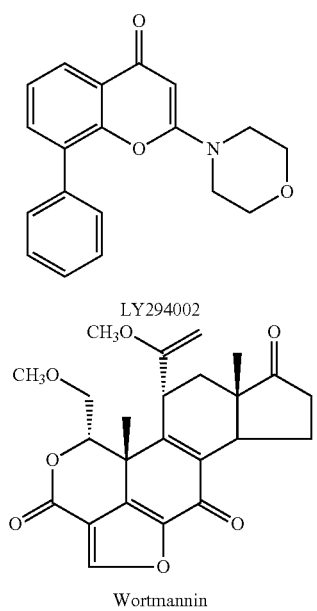

Based on studies with wortmannin, there is evidence that PI3 kinase function is also necessary for some aspects of leukocyte signalling by G protein-coupled receptors (Thelen et al., 1994, see above). In addition, it has been shown that wortmannin and LY294002 block neutrophil migration and superoxide release. Carboxygenase-inhibiting benzofuran derivatives are disclosed by John M. Janusz et al., in J. Med. Chem. 1998; Vol. 41, No. 18.

It is now well understood that deregulation of oncogenes and tumour-suppressor genes contributes to the formation of malignant tumours, for example by increasing cell growth and proliferation or increased cell survival. It is now also known that signalling pathways promoted by the PI3K family play a central role in a number of cell processes, such as, inter alia, in proliferation and survival, and deregulation of these pathways is a causative factor in a broad spectrum of human cancer diseases and other diseases (Katso et al., Annual Rev. Cell Dev. Biol, 2001, 17: 615-617, and Foster et al, J. Cell Science. 2003, U6: 3037-3040).

Class I PI3K is a heterodimer consisting of a catalytic p110 subunit and a regulatory subunit, and the family is further divided into class Ia and class Ib enzymes on the basis of the regulatory partners and the regulation mechanisms. Class Ia enzymes consist of three different catalytic subunits (p110α, p110β, and p110δ), which dimerise with five different regulatory subunits (p85α, p55α, p50α, p85β and p55γ), where all catalytic subunits are able to interact with all regulatory subunits to form various heterodimers. Class Ia PI3Ks are generally activated in response to growth factor stimulation of receptor tyrosine kinases via interaction of the regulatory SH2 domain subunit with specific phosphotyrosine residues of the activated receptor or adaptor proteins, such as IRS-1. Small GTPases (for example ras) are likewise involved in the activation of PI3K together with receptor tyrosine kinase activation. Both p110α and p110β are constitutively involved in all cell types, whereas p110δ expression is more restricted to leukocyte populations and some epithelial cells. By contrast, the only class Ib enzyme consists of a catalytic p110γ subunit, which interacts with a regulatory p101 subunit. In addition, the class Ib enzyme is activated by G protein-coupled receptor (GPCR) systems, and its expression appears to be limited to leukocytes.

There is now clear evidence showing that class Ia PI3K enzymes contribute to tumorigenesis in a large number of human cancer diseases, either directly or indirectly (Vivanco and Sawyers, Nature Reviews Cancer, 2002, 2, 489-501). For example, the p110α subunit is amplified in some tumours, such as, for example, in ovarian tumours (Shayesteh, et al., Nature Genetics, 1999, 21:99-102) and cervix (Ma et al, Oncogene, 2000, 19: 2739-2744). Recently, activating mutations in p110α (PIK3CA gene) have been associated with various other tumours, such as, for example, colon and breast and lung tumours (Samuels, et al., Science, 2004, 304, 554). Tumour-related mutations in p85α have likewise been identified in cancer diseases, such as ovarian and colon cancer (Philp et al., Cancer Research, 2001, 61, 7426-7429). Besides direct effects, activation of class I PI3Ks is probably involved in tumorigenic events occurring upstream of signalling pathways, for example by means of ligand-dependent or ligand-independent activation of receptor tyrosine kinases, GPCR systems or integrins (Vara et al., Cancer Treatment Reviews, 2004, 30, 193-204). Examples of such upstream signalling pathways include overexpression of the receptor tyrosine kinase Erb2 in a number of tumours which lead to activation of PI3K-promoted pathways (Harari et al., Oncogene, 2000, Jj), 6102-6114) and overexpression of the oncogene Ras (Kauffmann-Zeh et al., Nature, 1997, 385, 544-548). In addition, class Ia PI3Ks may contribute indirectly to tumorigenesis caused by various downstream signalling events. For example, the loss of function of the PTEN tumour-suppressor phosphatase which catalyses the conversion of $PI(3,4,5,)P_3$ back to $PI(4,5)P_2$ is associated with a very broad range of tumours via deregulation of the PI3K-promoted production of $PI(3,4,5)P_3$ (Simpson and Parsons, Exp. Cell Res., 2001, 264, 29-41). In addition, the increase in the effects of other PI3K-promoted signalling events probably contributes to a number of cancer diseases, for example by activation of AKT (Nicholson and Andeson, Cellular Signaling, 2002, 14, 381-395).

Besides a role in the promotion of proliferative and survival signalling in tumour cells, there is good evidence that class I PI3K enzymes also contribute to tumorigenesis via their function in tumour-associated stromal cells. PI3K signalling is known to play an important role in the promotion of angiogenic events in endothelial cells in response to pro-angiogenic factors, such as VEGF (abid et al., Arterioscler.

Thromb. Vasc. Biol., 2004, 24, 294-300). Since class I PI3K enzymes are also involved in mobility and migration (Sawyer, Expert Opinion investing. Drugs, 2004, 13, 1-19), PI3K inhibitors are thought to provide a therapeutic benefit via inhibition of tumour cell invasion and metastasis.

The synthesis of small compounds which specifically inhibit, regulate and/or modulate PI3 kinase signal transduction is therefore desirable and an aim of the present invention.

It has been found that the compounds according to the invention and salts thereof have very valuable pharmacological properties while being well tolerated.

It has been found that the compounds according to the invention are inhibitors of the phosphoinositide 3-kinases (PI3Ks).

The compounds according to the invention inhibit protein kinases, in particular PI3K, mTOR and DNA-PK. In addition, they activate Foxo3A translocation. If the phosphoinositide 3-kinase (PI3K) enzyme is inhibited by a compound according to the invention, PI3K is unable to exert its enzymatic, biological and/or pharmacological effects. The compounds according to the invention are therefore suitable for the treatment of autoimmune diseases, inflammatory diseases, cardiovascular diseases, neurodegenerative diseases, allergy, asthma, pancreatitis, multiorgan failure, kidney diseases, blood platelet aggregation, cancer, sperm motility, transplant rejection, graft rejection and lung injuries.

The compounds of the formula (I) are suitable, in particular, as medicaments for the treatment of autoimmune diseases, inflammatory diseases, cardiovascular diseases, neurodegenerative diseases, allergy, asthma, pancreatitis, multiorgan failure, kidney diseases, blood platelet aggregation, cancer, sperm motility, transplant rejection, graft rejection and lung injuries.

According to an embodiment of the present invention, the compounds of the formula (I) are inhibitors of one or more phosphatoinositide 3-kinases (PI3Ks), advantageously phosphatoinositide 3-kinase γ (PI3Kγ), phosphatoinositide 3-kinase α (PI3Kα), phosphatoinositide 3-kinase β (PI3Kβ), and/or phosphatoinositide 3-kinase δ (PI3K δ).

The compounds of the formula (I) are suitable for the modulation, in particular for the inhibition, of the activity of phosphatoinositide 3-kinases (PI3Ks), advantageously phosphatoinositide 3-kinase (PI3Kα). The compounds according to the invention are therefore also suitable for the treatment of disorders which are promoted by PI3Ks. The treatment includes the modulation—in particular the inhibition or downregulation—of phosphatoinositide 3-kinases.

The compounds according to the invention are preferably used for the preparation of a medicament for the treatment of a disorder selected from multiple sclerosis, psoriasis, rheumatoid arthritis, systemic lupus erythematosus, inflammatory bowel disease, lung inflammation, thrombosis or brain infection or inflammation, such as meningitis or encephalitis, Alzheimer's disease, Huntington's disease, CNS trauma, stroke or ischaemic states, cardiovascular diseases, such as atherosclerosis, cardiac hypertrophy, cardiac myocyte dysfunction, hypertension or vasoconstriction.

The compounds of the formula (I) are preferably suitable for the treatment of autoimmune diseases or inflammatory diseases, such as multiple sclerosis, psoriasis, rheumatoid arthritis, systemic lupus erythematosus, inflammatory bowel disease, lung inflammation, thrombosis or brain infection or inflammation, such as meningitis or encephalitis.

The compounds of the formula (I) are preferably suitable for the treatment of neurodegenerative diseases, such as, inter alia, multiple sclerosis, Alzheimer's disease, Huntington's disease, CNS trauma, stroke or ischaemic states.

The compounds of the formula (I) are preferably suitable for the treatment of cardiovascular diseases, such as atherosclerosis, cardiac hypertrophy, cardiac myocyte dysfunction, hypertension or vasoconstriction.

The compounds of the formula (I) are preferably suitable for the treatment of chronic obstructive pulmonary disease, anaphylactic shock fibrosis, psoriasis, allergic diseases, asthma, stroke, ischaemic states, ischemia-reperfusion, blood platelet aggregation or activation, skeletal muscle atrophy or hypertrophy, leukocyte recruitment in cancer tissue, angiogenesis, invasion metastasis, in particular melanoma, Karposi's sarcoma, acute and chronic bacterial and viral infections, sepsis, transplant rejection, graft rejection, glomerulosclerosis, glomerulonephritis, progressive renal fibrosis, endothelial and epithelial injuries in the lung, and lung airway inflammation.

Since the pharmaceutically active compounds of the present invention are active as PI3 kinase inhibitors, in particular the compounds which inhibit pI3Kα, either selectively or together with one or more of PI3Kδ, PI3Kβ and/or PI3Kγ, they have therapeutic utility in the treatment of cancer.

The invention preferably relates to a method for the treatment of cancer in a mammal, including humans, where the cancer is selected from: brain (gliomas), glioblastomas, leukaemias, Bannayan-Zonana syndrome, Cowden disease, Lhermitte-Duclos disease, breast cancer, inflammatory breast cancer, Wilm's tumour, Ewing's sarcoma, rhabdomyosarcoma, ependymoma, medulloblastoma, colon, head and neck, kidney, lung, liver, melanoma, ovary, pancreas, prostate, sarcoma, osteosarcoma, giant-cell tumour of bone and thyroid.

The invention preferably relates to a method for the treatment of cancer in a mammal, including humans, where the cancer is selected from: lymphoblastic T-cell leukaemia, chronic myelogenous leukaemia, chronic lymphocytic leukaemia, hairy-cell leukaemia, acute lymphoblastic leukaemia, acute myelogenous leukaemia, chronic neutrophilic leukaemia, acute lymphoblastic T-cell leukaemia, plasmacytoma, immunoblastic large cell leukaemia, mantle cell leukaemia, multiple myeloma, megakaryoblastic leukaemia, multiple myeloma, acute megakaryocytic leukaemia, promyelocytic leukaemia and erythroleukaemia.

The invention preferably relates to a method for the treatment of cancer in a mammal, including humans, where the cancer is selected from malignant lymphoma, Hodgkin's lymphoma, non-Hodgkin's lymphoma, lymphoblastic T-cell lymphoma, Burkitt's lymphoma and follicular lymphoma. The invention preferably relates to a method for the treatment of cancer in a mammal, including humans, where the cancer is selected from: neuroblastoma, bladder cancer, urothelial cancer, lung cancer, vulvar cancer, cervical cancer, endometrial cancer, renal cancer, mesothelioma, oesophageal cancer, salivary gland cancer, hepatocellular cancer, bowel cancer, nasopharyngeal cancer, buccal cancer, mouth cancer, GIST (gastrointestinal stromal tumour) and testicular cancer.

The compounds of the formula I can furthermore be used for the isolation and investigation of the activity or expression of PI3 kinase. In addition, they are particularly suitable for use in diagnostic methods for diseases in connection with unregulated or disturbed PI3 kinase activity.

It can be shown that the compounds according to the invention have an antiproliferative action in vivo in a xenotransplant tumour model. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both prevention of diseases and treatment of pre-existing conditions. The prevention of proliferation is achieved by administration of the compounds according to the invention prior to the development of overt disease, for example to prevent the growth of tumours, prevent metastatic growth, diminish restenosis associated with cardiovascular surgery, etc. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-González, R. and Glenney, Jr., J. R. 1992, J. Biol. Chem. 267, page 14535).

For the identification of kinase inhibitors, various assay systems are available. In scintillation proximity assay (Sorg et al., J. of Biomolecular Screening, 2002, 7, 11-19) and flashplate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., 2002, Biochem. J.).

PRIOR ART

Other heterocyclic PI3K inhibitors are described in WO 2009/046448 A1, WO 2008/157191 A2 and WO 2008/012326 A1.
Imidazol(on)e derivatives are disclosed in:
WO 2008/094556, WO 2005/105790, WO 2004/026859, WO 2 003/035638 and WO 9638421.
Pyrazine derivatives and the use thereof as PI3K inhibitors are disclosed in WO 2007/023186 A1.
Pyridopyrimidines are described in WO 2009/039140 A1 as PI3 kinase inhibitors.
Quinoxaline derivatives are disclosed in WO 2008/127594 as PI3K inhibitors.

SUMMARY OF THE INVENTION

The invention relates to compounds of the formula I

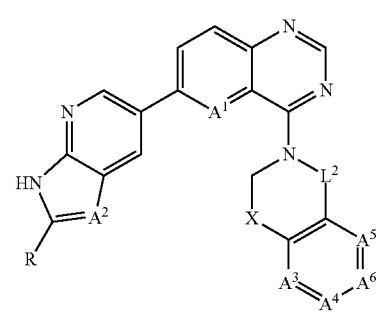

in which
$A^1$ denotes N or $CR^1$,
$A^2$ denotes N or $CR^2$,
$A^3$, $A^4$,
$A^5$, $A^6$ each, independently of one another, denote N or $CR^3$,
X is absent or denotes unbranched or branched alkylene having 1-10 C atoms, in which 1-7 H atoms may be replaced by OH, F and/or Cl,
and/or in which one or two non-adjacent CH and/or $CH_2$ groups may be replaced by O, N, NH, NA', CO, S, SO, $SO_2$, OCO, NHCONH, NHCO, $NHSO_2$, COO, CONH and/or CH=CH groups, or cycloalkylene having 3-7 C atoms,
$L^2$ is absent or denotes unbranched or branched alkylene having 1-10 C atoms, in which 1-7 H atoms may be replaced by OH, F and/or Cl,
and/or in which one or two non-adjacent CH and/or $CH_2$ groups may be replaced by O, N, NH, NA', CO, S, SO, $SO_2$, OCO, NHCONH, NHCO, $NHSO_2$, COO, CONH and/or CH=CH groups, or cycloalkylene having 3-7 C atoms,
with the proviso that X and $L^2$ cannot be absent simultaneously,
R denotes H or unbranched or branched alkyl having 1-10 C atoms, in which 1-7 H atoms may be replaced by F and/or Cl and/or in which one or two non-adjacent CH and/or $CH_2$ groups may be replaced by O, N, NH, NA', CO, S, SO, $SO_2$, OCO, NHCONH, NHCO, $NHSO_2$, COO, CONH and/or CH=CH groups, or cyclic alkyl having 3-7 C atoms, $R^1$ denotes H or unbranched or branched alkyl having 1-10 C atoms, in which 1-7H atoms may be replaced by F and/or Cl and/or in which one or two non-adjacent CH and/or $CH_2$ groups may be replaced by O, N, NH, NA', CO, S, SO, $SO_2$, OCO, NHCONH, NHCO, $NHSO_2$, COO, CONH and/or CH=CH groups, or cyclic alkyl having 3-7 C atoms, $R^2$ denotes H or unbranched or branched alkyl having 1-10 C atoms, in which 1-7H atoms may be replaced by F and/or Cl and/or in which one or two non-adjacent CH and/or $CH_2$ groups may be replaced by O, N, NH, NA', CO, S, SO, $SO_2$, OCO, NHCONH, NHCO, $NHSO_2$, COO, CONH and/or CH=CH groups, or cyclic alkyl having 3-7 C atoms, $R^3$ denotes H or unbranched or branched alkyl having 1-10 C atoms, in which 1-7H atoms may be replaced by F and/or Cl and/or in which one or two non-adjacent CH and/or $CH_2$ groups may be replaced by O, N, NH, NA', CO, S, SO, $SO_2$, OCO, NHCONH, NHCO, $NHSO_2$, COO, CONH and/or CH=CH groups, or cyclic alkyl having 3-7 C atoms, A' in each case, independently of one another, denotes unbranched or branched alkyl having 1-10 C atoms, in which 1-7H atoms may be replaced by F and/or Cl, and/or in which one or two non-adjacent CH and/or $CH_2$ groups may be replaced by O, N, NH, NA, S, SO, $SO_2$ and/or CH=CH groups, or cyclic alkyl having 3-7 C atoms, A denotes alkyl having 1, 2, 3 or 4 C atoms, and pharmaceutically usable salts, tautomers and stereoisomers thereof, including mixtures thereof in all ratios, Compounds of the formula I are also taken to mean the hydrates and solvates of these compounds, furthermore pharmaceutically usable derivatives.

The invention also relates to the optically active forms (stereoisomers), the enantiomers, the racemates, the diastereomers and the hydrates and solvates of these compounds. solvates of the compounds are taken to mean adductions of inert solvent molecules onto the compounds which form owing to their mutual attractive force. Solvate are, for example, mono- or dihydrates or alcoholates. The invention naturally also encompasses the solvates of the salts of the compounds according to the invention. Pharmaceutically usable derivatives are taken to mean, for example, the salts of the compounds according to the invention and also so-called prodrug compounds.

Prodrug derivatives are taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active compound which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side effects or also the reduction in the advance of a disease, complaint or disorder.

The term "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I and pharmaceutically usable salts, tautomers and stereoisomers thereof, characterised in that a) a compound of the formula II

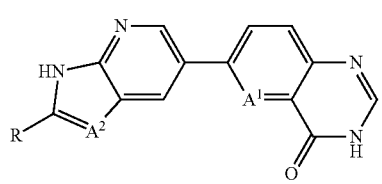

in which R, $A^1$ and $A^2$ have the meanings indicated in claim 1, is reacted with a compound of the formula III

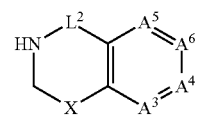

in which X, $L^2$, $A^3$, A4, $A^5$ and $A^6$ have the meanings indicated in claim 1, or b) a compound of the formula IV

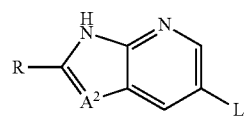

in which R and $A^2$ have the meanings indicated in claim 1 and

L denotes a boronic acid or boronic acid ester radical, is reacted with a compound of the formula V

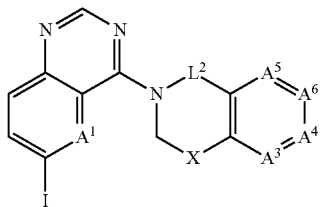

in which X, $L^2$, $A^1$, $A^3$, $A^4$, $A^5$ and $A^6$ have the meanings indicated in claim 1,
and/or
a base or acid of the formula I is converted into one of its salts.

Above and below, the radicals R, X, $L^2$ and $A^1$-$A^6$ have the meanings indicated in the case of the formula I, unless expressly indicated otherwise.

A' denotes alkyl, is unbranched (linear) or branched, and has 1, 2, 3, 4, 5, 6, 7, 8, 9 or 10 C atoms. A' preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A' very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

A' preferably also denotes unbranched or branched alkyl having 1-6 C atoms, in which, in addition, one or two $CH_2$ groups may be replaced by O. A' therefore preferably also denotes methoxy, 2-hydroxyethyl or 2-methoxyethyl.

A denotes alkyl, is unbranched (linear) or branched, and has 1, 2, 3 or 4 C atoms.

Cyclic alkyl (cycloalkyl) preferably denotes cyclopropyl, cyclobutyl, cylopentyl, cyclohexyl or cycloheptyl.

X preferably denotes "absent" (a bond) or unbranched or branched alkylene having 1-4 C atoms (preferably methylene, ethylene, propylene or butylene), and in which one $CH_2$ group may be replaced by O, NH, CO or $SO_2$.

Thus, X denotes, for example, $CH_2O$, $OCH_2$, $CH_2CO$ or $COCH_2$.

$L^2$ preferably denotes "absent" (a bond) or unbranched or branched alkylene having 1-4 C atoms (preferably methylene, ethylene, propylene or butylene).

R preferably denotes H or unbranched or branched alkyl having 1, 2, 3 or 4 C atoms.

R particularly preferably denotes H or methyl, ethyl, propyl, isopropyl, butyl, isobutyl, sec-butyl, tert-butyl.

$R^1$ preferably denotes H.
$R^2$ preferably denotes H.
$R^3$ preferably denotes H or unbranched or branched alkyl having 1, 2, 3 or 4 C atoms, such as methyl, ethyl, propyl, isopropyl, butyl, isobutyl, sec-butyl, tert-butyl, and in which one $CH_2$ group may be replaced by O. Thus, $R^3$ preferably also denotes methoxy, 2-hydroxyethyl or 2-methoxyethyl.

Hal preferably denotes F, Cl or Br, but also I, particularly preferably F or Cl. Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Ii, which conform to the formula I and in which the radicals not designated in greater detail have the meaning indicated for the formula I, but in which in Ia $A^3$, $A^4$, $A^5$, $A^6$ denotes $CR^3$;
in Ib X is absent or denotes unbranched or branched alkylene having 1-4 C atoms,
and in which one $CH_2$ group may be replaced by O, NH, CO or $SO_2$;
in Ic $L^2$ is absent or denote unbranched or branched alkylene having 1-4 C atoms;
in Id R denotes H or unbranched or branched alkyl having 1-4 C atoms;
in Ie $R^1$ denotes H;
in If $R^2$ denotes H;
in Ig $R^3$ denotes H or unbranched or branched alkyl having 1-4 C atoms and in which one $CH_2$ group may be replaced by O;
in 1 h $A^1$ denotes N or $CR^1$,
$A^2$ denotes N or $CR^2$,
$A^3$, $A^4$, $A^5$, $A^6$ denote $CR^3$,
X is absent or denotes unbranched or branched alkylene having 1-4 C atoms,
and in which one $CH_2$ group may be replaced by O, NH, CO or $SO_2$,
$L^2$ is absent or denotes unbranched or branched alkylene having 1-4 C atoms,
R denotes H or unbranched or branched alkyl having 1-4 C atoms,
$R^1$ denotes H,
$R^2$ denotes H,
$R^3$ denotes H or unbranched or branched alkyl having 1-4 C atoms and in which one $CH_2$ group may be replaced by O;

and pharmaceutically usable salts, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

Compounds of the formula I can preferably be obtained by reacting a compound of the formula II with a compound of the formula III.

The starting compounds of the formulae II and III are generally known. If they are novel, however, they can be prepared by methods known per se. Depending on the conditions used, the reaction time is between a few minutes and 14 days, the reaction temperature is between about −30° and 140°, normally between 0° and 100°, in particular between about 60° and about 90°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to acetonitrile and/or DMF.

The reaction is preferably carried out with addition of benzotriazol-1-yloxy)tris-(dimethylamino)phosphonium hexafluorophosphate (BOP) and an organic base, preferably 1,8-diazabicyclo[5.4.0]undec-7-ene (DBU).

Compounds of the formula I can furthermore preferably be obtained by reacting a compound of the formula IV with a compound of the formula V.

The reaction is generally carried out under conditions as are known to the person skilled in the art for a Suzuki reaction.

The starting compounds of the formulae IV and V asre generally known. If they are novel, however, they can be prepared by methods known per se. In the compounds of the formula IV, L preferably denotes

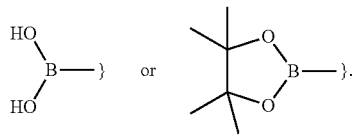

The reaction is carried out under standard conditions of a Suzuki coupling. Depending on the conditions used, the reaction time is between a few minutes and 14 days, the reaction temperature is between about −30° and 140°, normally between 0° and 100°, in particular between about 60° and about 90°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to ethanol, toluene, dimethoxyethane.

The compounds of the formulae I can furthermore be obtained by liberating them from their functional derivatives.

Preferred starting materials are those which contain corresponding protected amino and/or hydroxyl groups instead of one or more free amino and/or hydroxyl groups, preferably those which carry an amino-protecting group instead of an H atom bonded to an N atom, for example those which conform to the formula I, but contain an NR' or NHR' group (in which R' denotes an amino-protecting group, for example triisopropylsilyl) instead of an NH or $NH_2$ group.

Silyl protecting groups are preferably cleaved off in the presence of fluoride ions under standard conditions.

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut, Pbf, Pmc and Mtr groups can, for example, preferably be cleaved off using TFA in dichloromethane or using approximately 3 to 5 N HCl in dioxane at 15-30°, the FMOC group can be cleaved off using an approximately 5 to 50% solution of dimethylamine, diethylamine or piperidine in DMF at 15-30°.

Hydrogenolytically removable protecting groups (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; $di(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active compound which comprises a compound of the formula I in the form of one of its salts, in particular if this salt form imparts improved pharmacokinetic properties on the active compound compared with the free form of the active compound or any other salt form of the active compound used earlier. The pharmaceutically acceptable salt form of the active compound can also provide this active compound for the first time with a desired pharmacokinetic property which it did not have earlier and can even have a positive influence on the pharmacodynamics of this active compound with respect to its therapeutic efficacy in the body.

The invention furthermore relates to medicaments comprising at least one compound of the formula I and/or pharmaceutically usable salts and stereoisomers thereof, including mixtures thereof in all ratios, and optionally excipients and/or adjuvants.

Pharmaceutical formulations can be administered in the form of dosage units which comprise a predetermined amount of active compound per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active compound per dosage unit. Preferred dosage unit formulations are those which comprise a daily dose or part-dose, as indicated above, or a corresponding fraction thereof of an active compound. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active compound with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units. Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active compound can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active compound can be employed either with a paraffinic or a water-miscible cream base. Alternatively, the active compound can be formulated to give a cream with an oil-in-water cream base or a water-in-oil base.

Pharmaceutical formulations adapted for topical application to the eye include eye drops, in which the active compound is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or pharmaceutically usable salts and stereoisomers thereof, including mixtures thereof in all ratios, and at least one further medicament active compound.

The invention also relates to a set (kit) consisting of separate packs of (a) an effective amount of a compound of the formula I and/or pharmaceutically usable salts and stereoisomers thereof, including mixtures thereof in all ratios,
and
(b) an effective amount of a further medicament active compound.

The set comprises suitable containers, such as boxes, individual bottles, bags or ampoules. The set may, for example, comprise separate ampoules, each containing an effective amount of a compound of the formula I and/or pharmaceutically usable salts and stereoisomers thereof, including mixtures thereof in all ratios,
and an effective amount of a further medicament active compound in dissolved or lyophilised form.

Use

The present compounds are suitable as pharmaceutical active compounds for mammals, especially for humans, in the treatment of diseases.

The present invention encompasses the compounds of the formula I for use in the treatment or prevention of autoimmune diseases, inflammatory diseases, cardiovascular diseases, neurodegenerative diseases, allergy, asthma, pancreatitis, multiorgan failure, kidney diseases, blood platelet aggregation, cancer, sperm motility, transplant rejection, graft rejection and lung injuries.

The present invention encompasses the use of the compounds of the formula I and/or physiologically acceptable salts thereof for the preparation of a medicament for the treatment or prevention of autoimmune diseases, inflammatory diseases, cardiovascular diseases, neurodegenerative diseases, allergy, asthma, pancreatitis, multiorgan failure, kidney diseases, blood platelet aggregation, cancer, sperm motility, transplant rejection, graft rejection and lung injuries.

The compounds according to the invention are preferably used for the preparation of a medicament for the treatment of a disorder selected from multiple sclerosis, psoriasis, rheumatoid arthritis, systemic lupus erythematosus, inflammatory bowel disease, lung inflammation, thrombosis or brain infection or inflammation, such as meningitis or encephalitis, Alzheimer's disease, Huntington's disease, CNS trauma, stroke, or ischaemic states, cardiovascular diseases, such as atherosclerosis, cardiac hypertrophy, cardiac myocyte dysfunction, hypertension or vasoconstriction.

The present invention encompasses the use of the compounds of the formula I and/or physiologically acceptable salts thereof for the preparation of a medicament for the treatment or prevention of autoimmune diseases or inflammatory diseases, such as multiple sclerosis, psoriasis, rheumatoid arthritis, systemic lupus erythematosus, inflammatory bowel disease, lung inflammation, thrombosis or brain infection or inflammation, such as meningitis or encephalitis.

The present invention encompasses the use of the compounds of the formula I and/or physiologically acceptable salts thereof for the preparation of a medicament for the treatment or prevention of neurodegenerative diseases, such as, inter alia, multiple sclerosis, Alzheimer's disease, Huntington's disease, CNS trauma, stroke or ischaemic states.

The present invention encompasses the use of the compounds of the formula I and/or physiologically acceptable salts thereof for the preparation of a medicament for the treatment or prevention of cardiovascular diseases, such as atherosclerosis, cardiac hypertrophy, cardiac myocyte dysfunction, hypertension or vasoconstriction.

The present invention encompasses the use of the compounds of the formula I and/or physiologically acceptable salts thereof for the preparation of a medicament for the treatment or prevention of chronic obstructive pulmonary disease, anaphylactic shock fibrosis, psoriasis, allergic diseases, asthma, stroke, ischaemic states, ischemia-reperfusion, blood platelet aggregation or activation, skeletal muscle atrophy or hypertrophy, leukocyte recruitment in cancer tissue, angiogenesis, invasion metastasis, in particular melanoma, Karposi's sarcoma, acute and chronic bacterial and viral infections, sepsis, transplant rejection, graft rejection, glomerulosclerosis, glomerulonephritis, progressive renal fibrosis, endothelial and epithelial injuries in the lung, and lung airway inflammation.

The present invention encompasses the use of the compounds of the formula I and/or physiologically acceptable salts thereof for the preparation of a medicament for the treatment or prevention of cancer in a mammal, including humans, where the cancer is selected from: brain (gliomas), glioblastomas, leukaemias, Bannayan-Zonana syndrome, Cowden disease, Lhermitte-Duclos disease, breast cancer, inflammatory breast cancer, Wilm's tumour, Ewing's sarcoma, rhabdomyosarcoma, ependymoma, medulloblastoma, colon, head and neck, kidney, lung, liver, melanoma, ovary, pancreas, prostate, sarcoma, osteosarcoma, giant-cell tumour of bone and thyroid.

The present invention encompasses the use of the compounds of the formula I and/or physiologically acceptable salts thereof for the preparation of a medicament for the treatment or prevention of cancer in a mammal, including humans, where the cancer is selected from: lymphoblastic T-cell leukaemia, chronic myelogenous leukaemia, chronic lymphocytic leukaemia, hairy-cell leukaemia, acute lymphoblastic leukaemia, acute myelogenous leukaemia, chronic neutrophilic leukaemia, acute lymphoblastic T-cell leukaemia, plasmacytoma, immunoblastic large cell leukaemia, mantle cell leukaemia, multiple myeloma, megakaryoblastic leukaemia, multiple myeloma, acute megakaryocytic leukaemia, promyelocytic leukaemia and erythroleukaemia.

The present invention encompasses the use of the compounds of the formula I and/or physiologically acceptable salts thereof for the preparation of a medicament for the treatment or prevention of cancer in a mammal, including humans, where the cancer is selected from malignant lymphoma, Hodgkin's lymphoma, non-Hodgkin's lymphoma, lymphoblastic T-cell lymphoma, Burkitt's lymphoma and follicular lymphoma.

The invention preferably relates to a method for the treatment of cancer in a mammal, including humans, where the cancer is selected from: neuroblastoma, bladder cancer, urothelial cancer, lung cancer, vulvar cancer, cervical cancer, endometrial cancer, renal cancer, mesothelioma, oesophageal cancer, salivary gland cancer, hepatocellular cancer, bowel cancer, nasopharyngeal cancer, buccal cancer, mouth cancer, GIST (gastrointestinal stromal tumour) and testicular cancer.

The compounds of the formula I can furthermore be used in order to provide additive or synergistic effects in certain existing cancer chemotherapies, and/or can be used in order to restore the efficacy of certain existing cancer chemotherapies and radiotherapies.

Also encompassed is the use of the compounds of the formula I and/or physiologically acceptable salts thereof for the preparation of a medicament in a mammal, where a therapeutically effective amount of a compound according to the invention is administered. The therapeutic amount varies according to the specific disease and can be determined by the person skilled in the art without undue effort.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic/DNA-damaging agents and combinations thereof, as used in medical oncology, such as alkylating agents (for example cis-platin, carboplatin, cyclophosphamide, nitrogen mustard, melphalan, chloroambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines, like adriamycin, bleomycin, doxorubicin, daunomycin, epirubicin, idarubicin, mitomycin-C, dactinomycin and mithramycin); antimitotic agents (for example vincan alkaloids, like vincristine, vinblastine, vindesine and vinorelbine, and taxoids, like taxol and taxotere); topoisomerase inhibitors (for example epipodophyllotoxins, like etoposide and teniposide, amsacrine, topotecan, irinotecan and camptothecin) and cell-differentiating agents (for example all-trans-retinoic acid, 13-cis-retinoic acid and fenretinide);

(ii) cytostatic agents, such as antioestrogens (for example tamoxifen, toremifene, raloxifene, droloxifene and iodoxyfene), oestrogen receptor downregulators (for example fulvestrant), antiandrogens (for example bicalutamide, flutamide, nilutamide and cyproterone acetate), LHRH antagonists or LHRH agonists (for example goserelin, leuprorelin and buserelin), progesterones (for example megestrol acetate), aromatase inhibitors (for example as anastrozole, letrozole, vorazole and exemestane) and inhibitors of 5α-reductase, such as finasteride;

(iii) agents which inhibit cancer cell invasion (for example metallo-proteinase inhibitors, like marimastat, and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbbl antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy) quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholino-propoxy)-quinazolin-4-amine (Cl 1033)), for example inhibitors of the platelet-derived growth factor family and for example inhibitors of the hepatocyte growth factor family;

(v) antiangiogenic agents, such as those which inhibit the effects of vascular endothelial growth factor, (for example the anti-vascular endothelial cell growth factor antibody bevacizumab [Avastin™], compounds such as those disclosed in published international patent applications WO 97/22596, WO 97/30035, WO 97/32856 and WO 98/13354) and compounds that work by other mechanisms (for example linomide, inhibitors of integrin αvβ3 function and angiostatin);

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-Ras antisense;

(viii) gene therapy approaches, including, for example, approaches for replacement of aberrant genes, such as aberrant p53 or aberrant BRCA1 or BRCA2, GDEPT (gene-directed enzyme pro-drug therapy) approaches, such as those using cytosine deaminase, thymidine kinase or a bacterial nitroreductase enzyme, and approaches for increasing patient tolerance to chemotherapy or radiotherapy, such as multi-drug resistance gene therapy; and (ix) immunotherapy approaches, including, for example, ex-vivo and in-vivo approaches for increasing the immunogenicity of patient tumour cells, such as transfection with cytokines, such as interleukin 2, interleukin 4 or granulocyte-macrophage colony stimulating factor, approaches for decreasing T-cell anergy, approaches using transfected immune cells, such as cytokine-transfected dendritic cells, approaches using cytokine-transfected tumour cell lines, and approaches using anti-idiotypic antibodies.

The medicaments from Table 1 below are preferably, but not exclusively, combined with the compounds of the formula I.

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aeterna) |
| | Carboxyphthalatoplatinum | Satraplatin (Johnson Matthey) |
| | Tetraplatin | BBR-3464 (Hoffmann- |
| | Ormiplatin | La Roche) |
| | Iproplatin | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-Ethyl-10-hydroxy-camptothecin | TAS-103 (Taiho) |
| | Topotecan | Elsamitrucin (Spectrum) |
| | Dexrazoxanet (TopoTarget) | J-107088 (Merck & Co) |
| | Pixantrone (Novuspharma) | BNP-1350 (BioNumerik) |
| | Rebeccamycin analogue (Exelixis) | CKD-602 (Chong Kun Dang) |
| | | KW-2170 (Kyowa Hakko) |
| | BBR-3576 (Novuspharma) | |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | Epirubicin | Bleomycin sulfate (Blenoxan) |
| | Therarubicin | Bleomycinic acid |
| | Idarubicin | Bleomycin A |
| | Rubidazon | Bleomycin B |
| | Plicamycinp | Mitomycin C |
| | Porfiromycin | MEN-10755 (Menarini) |
| | Cyanomorpholinodoxorubicin | GPX-100 (Gem Pharmaceuticals) |
| | Mitoxantron (Novantron) | |
| Antimitotic agents | Paclitaxel | SB 408075 (GlaxoSmithKline) |
| | Docetaxel | E7010 (Abbott) |

TABLE 1-continued

| | | |
|---|---|---|
| | Colchicine | PG-TXL (Cell Therapeutics) |
| | Vinblastine | IDN 5109 (Bayer) |
| | Vincristine | A 105972 (Abbott) |
| | Vinorelbine | A 204197 (Abbott) |
| | Vindesine | LU 223651 (BASF) |
| | Dolastatin 10 (NCI) | D 24851 (ASTA Medica) |
| | Rhizoxin (Fujisawa) | ER-86526 (Eisai) |
| | Mivobulin (Warner-Lambert) | Combretastatin A4 (BMS) |
| | Cemadotin (BASF) | Isohomohalichondrin-B |
| | RPR 109881A (Aventis) | (PharmaMar) |
| | TXD 258 (Aventis) | ZD 6126 (AstraZeneca) |
| | Epothilone B (Novartis) | PEG-Paclitaxel (Enzon) |
| | T 900607 (Tularik) | AZ10992 (Asahi) |
| | T 138067 (Tularik) | !DN-5109 (Indena) |
| | Cryptophycin 52 (Eli Lilly) | AVLB (Prescient |
| | Vinflunine (Fabre) | NeuroPharma) |
| | Auristatin PE (Teikoku | Azaepothilon B (BMS) |
| | Hormone) | BNP-7787 (BioNumerik) |
| | BMS 247550 (BMS) | CA-4-prodrug (OXiGENE) |
| | BMS 184476 (BMS) | Dolastatin-10 (NrH) |
| | BMS 188797 (BMS) | CA-4 (OXiGENE) |
| | Taxoprexin (Protarga) | |
| Aromatase | Aminoglutethimide | Exemestan |
| inhibitors | Letrozole | Atamestan (BioMedicines) |
| | Anastrazole | YM-511 (Yamanouchi) |
| | Formestan | |
| Thymidylate synthase | Pemetrexed (Eli Lilly) | Nolatrexed (Eximias) |
| inhibitors | ZD-9331 (BTG) | CoFactor ™ (BioKeys) |
| DNA antagonists | Trabectedin (PharmaMar) | Mafosfamide (Baxter |
| | Glufosfamide (Baxter | International) |
| | International) | Apaziquone (Spectrum |
| | Albumin + 32P (Isotope | Pharmaceuticals) |
| | Solutions) | O6-benzylguanine (Paligent) |
| | Thymectacin (NewBiotics) | |
| | Edotreotid (Novartis) | |
| Farnesyl transferase | Arglabin (NuOncology Labs) | Tipifarnib (Johnson & |
| inhibitors | lonafarnib (Schering-Plough) | Johnson) |
| | BAY-43-9006 (Bayer) | Perillyl alcohol (DOR |
| | | BioPharma) |
| Pump inhibitors | CBT-1 (CBA Pharma) | Zosuquidar trihydrochloride |
| | Tariquidar (Xenova) | (Eli Lilly) |
| | MS-209 (Schering AG) | Biricodar dicitrate (Vertex) |
| Histone | Tacedinaline (Pfizer) | Pivaloyloxymethyl butyrate |
| acetyl-transferase | SAHA (Aton Pharma) | (Titan) |
| inhibitors | MS-275 (Schering AG) | Depsipeptide (Fujisawa) |
| Metalloproteinase | Neovastat (Aeterna Laboratorie | CMT-3 (CollaGenex) |
| inhibitors | Marimastat (British Biotech) | BMS-275291 (Celltech) |
| Ribonucleoside | Gallium maltolate (Titan) | Tezacitabine (Aventis) |
| reductase | Triapin (Vion) | Didox (Molecules for Health) |
| inhibitors | | |
| TNF-alpha | Virulizin (Lorus Therapeutics) | Revimid (Celgene) |
| agonists/antagonists | CDC-394 (Celgene) | |
| Endothelin-A | Atrasentan (Abbot) | YM-598 (Yamanouchi) |
| receptor antagonists | ZD-4054 (AstraZeneca) | |
| Retinoic acid | Fenretinide (Johnson & | Alitretinoin (Ligand) |
| receptor agonists | Johnson) | |
| | LGD-1550 (Ligand) | |
| Immunomodulators | Interferon | Dexosome therapy (Anosys) |
| | Oncophage (Antigenics) | Pentrix (Australian Cancer |
| | GMK (Progenics) | Technology) |
| | Adenocarcinoma vaccine | JSF-154 (Tragen) |
| | (Biomira) | Cancer vaccine (Intercell) |
| | CTP-37 (AVI BioPharma) | Norelin (Biostar) |
| | JRX-2 (Immuno-Rx) | BLP-25 (Biomira) |
| | PEP-005 (Peplin Biotech) | MGV (Progenics) |
| | Synchrovax vaccines (CTL | !3-Alethin (Dovetail) |
| | Immuno) | CLL-Thera (Vasogen) |
| | Melanoma vaccine (CTL | |
| | Immuno) | |
| | p21-RAS vaccine (GemVax) | |
| Hormonal and | Oestrogens | Prednisone |
| antihormonal agents | Conjugated oestrogens | Methylprednisolone |
| | Ethynyloestradiol | Prednisolone |
| | chlorotrianisene | Aminoglutethimide |
| | Idenestrol | Leuprolide |
| | Hydroxyprogesterone caproate | Goserelin |
| | Medroxyprogesterone | Leuporelin |
| | Testosterone | Bicalutamide |
| | Testosterone propionate | Flutamide |
| | Fluoxymesterone | Octreotide |

TABLE 1-continued

| Category | | |
|---|---|---|
| | Methyltestosterone | Nilutamide |
| | Diethylstilbestrol | Mitotan |
| | Megestrol | P-04 (Novogen) |
| | Tamoxifen | 2-Methoxyoestradiol |
| | Toremofin | (EntreMed) |
| | Dexamethasone | Arzoxifen (Eli Lilly) |
| Photodynamic agents | Talaporfin (Light Sciences) | Pd-bacteriopheophorbide (Yeda) |
| | Theralux (Theratechnologies) | Lutetium-Texaphyrin (Pharmacyclics) |
| | Motexafin-Gadolinium (Pharmacyclics) | Hypericin |
| Tyrosine kinase inhibitors | Imatinib (Novartis) | Kahalide F (PharmaMar) |
| | Leflunomide (Sugen/Pharmacia) | CEP-701 (Cephalon) |
| | ZDI839 (AstraZeneca) | CEP-751 (Cephalon) |
| | Erlotinib (Oncogene Science) | MLN518 (Millenium) |
| | Canertjnib (Pfizer) | PKC412 (Novartis) |
| | Squalamine (Genaera) | Phenoxodiol O |
| | SU5416 (Pharmacia) | Trastuzumab (Genentech) |
| | SU6668 (Pharmacia) | C225 (ImClone) |
| | ZD4190 (AstraZeneca) | rhu-Mab (Genentech) |
| | ZD6474 (AstraZeneca) | MDX-H210 (Medarex) |
| | Vatalanib (Novartis) | 2C4 (Genentech) |
| | PKI166 (Novartis) | MDX-447 (Medarex) |
| | GW2016 (GlaxoSmithKline) | ABX-EGF (Abgenix) |
| | EKB-509 (Wyeth) | IMC-1C11 (ImClone) |
| | EKB-569 (Wyeth) | |
| Various agents | SR-27897 (CCK-A inhibitor, Sanofi-Synthelabo) | BCX-1777 (PNP inhibitor, BioCryst) |
| | Tocladesine (cyclic AMP agonist, Ribapharm) | Ranpirnase (ribonuclease stimulant, Alfacell) |
| | Alvocidib (CDK inhibitor, Aventis) | Galarubicin (RNA synthesis inhibitor, Dong-A) |
| | CV-247 (COX-2 inhibitor, Ivy Medical) | Tirapazamine (reducing agent, SRI International) |
| | P54 (COX-2 inhibitor, Phytopharm) | N-Acetylcysta (reducing agent, Zambon) |
| | CapCell™ (CYP450 stimulant, Bavarian Nordic) | R-Flurbiprofen (NF-kappaB inhibitor, Encore) |
| | GCS-IOO (gal3 antagonist, GlycoGenesys) | 3CPA (NF-kappaB inhibitor, Active Biotech) |
| | G17DT immunogen (gastrin inhibitor, Aphton) | Seocalcitol (vitamin D receptor agonist, Leo) |
| | Efaproxiral (oxygenator, Allos Therapeutics) | 131-I-TM-601 (DNA antagonist, TransMolecular) |
| | PI-88 (heparanase inhibitor, Progen) | Eflornithin (ODC inhibitor, ILEX Oncology) |
| | Tesmilifen (histamine antagonist, YM BioSciences) | Minodronic acid (osteoclast inhibitor, Yamanouchi) |
| | Histamine (histamine H2 receptor agonist, Maxim) | Indisulam (p53 stimulant, Eisai) |
| | Tiazofurin (IMPDH inhibitor, Ribapharm) | Aplidine (PPT inhibitor, PharmaMar) |
| | Cilengitide (integrin antagonist, Merck KGaA) | Rituximab (CD20 antibody, Genentech) |
| | SR-31747 (IL-1 antagonist, Sanofi-Synthelabo) | Gemtuzumab (CD33 antibody, Wyeth Ayerst) |
| | CCI-779 (mTOR kinase inhibitor, Wyeth) | PG2 (haematopoiesis promoter, Pharmagenesis) |
| | Exisulind (PDE-V inhibitor, Cell Pathways) | Immunol™ (triclosan mouthwash, Endo) |
| | CP-461 (PDE-V inhibitor, Cell Pathways) | Triacetyluridine (uridine prodrug, Wellstat) |
| | AG-2037 (GART inhibitor, Pfizer) | SN-4071 (sarcoma agent, Signature BioScience) |
| | WX-UK1 (plasminogen activator inhibitor, Wilex) | TransMID-107™ (immunotoxin, KS Biomedix) |
| | PBI-1402 (PMN stimulant, ProMetic LifeSciences) | PCK-3145 (apoptosis promoter, Procyon) |
| | Bortezomib (proteasome inhibitor, Millennium) | Doranidazole (apoptosis promoter, Pola) |
| | SRL-172 (T-cell stimulant, SR Pharma) | CHS-828 (cytotoxic agent, Leo) |
| | TLK-286 (glutathione-S transferase inhibitor, Telik) | trans-Retinoic acid (differentiator, NIH) |
| | PT-100 (growth factor agonist, Point Therapeutics) | MX6 (apoptosis promoter, MAXIA) |
| | Midostaurin (PKC inhibitor, Novartis) | Apomine (apoptosis promoter, ILEX Oncology) |
| | Bryostatin-1 (PKC stimulant, GPC Biotech) | Urocidine (apoptosis promoter, Bioniche) |

TABLE 1-continued

CDA-II (apoptosis promoter, Everlife)
SDX-101 (apoptosis promoter, Salmedix)
Ceflatonin (apoptosis promoter, ChemGenex)
Ro-31-7453 (apoptosis promoter, La Roche)
Brostallicin (apoptosis promoter, Pharmacia)

A combined treatment of this type can be achieved with the aid of simultaneous, consecutive or separate dispensing of the individual components of the treatment. Combination products of this type employ the compounds according to the invention.

Assays

The compounds of the formula I described in the examples were tested in the assays described below, and it was found that they have a kinase-inhibiting activity. Other assays are known from the literature and could readily be performed by the person skilled in the art (see, for example, Dhana-bal et al., *Cancer Res.* 59:189-197; Xin et al., *J. Biol. Chem.* 274: 9116-9121; Sheu et al., *Anticancer Res.* 18:4435-4441; Ausprunk et al., *Dev. Biol.* 38:237-248; Gimbrone et al., *J. Natl. Cancer Inst.* 52:413-427; Nicosia et al., *In Vitro* 18:538-549).

Description of the Method for the Cellular Testing of PI3K Inhibitors

The measure used for the cellular PI3K activity is the PI3K-dependent phosphorylation of PKB at Serin 473. The cellular assay for determination of the P-S473-PKB level is carried out as a Luminex assay in 96-well format in PC3 cells. PC3 cells exhibit constitutive phosphorylation of PKB owing to a PTEN mutation.

PC3 cells are sown out with 20,000 cells per well in 100 µl medium (45% RPMI1460/45% Ham's F12/10% FCS) and incubated on the following day for 30 min with a serial dilution of the test substance (7 concentrations) under serum-free conditions. The cells are subsequently lysed using 90 µl of lysis buffer (20 mM Tris/HCl pH 8.0, 150 mM NaCl, 1% NP40, 10% glycerol, 1% phosphatase inhibitor I, 1% phosphatase inhibitor II, 0.1% protease inhibitor cocktail III, 0.01% benzonase) per well, and the lysates are separated off from insoluble cell constituents by means of centrifugation through a 96-well filter plate (0.65 µm). The lysates are incubated overnight at 4° C. with shaking with Luminex beads to which an anti-total PKB antibody is coupled. The detection is carried out on the following day by addition of a P-S473-PKB antibody and a species-specific PE-labelled secondary antibody. The detection of P-S473-PKB is carried out by measurement in a Luminex100 instrument by determination of 100 events per cavity in a measurement time of 60 sec. As pharmacological blank, the signals obtained from cells which have been treated with 3 µM wortmannin are subtracted from all other preparations. The control value used for maximum phosphorylation of PKB at S473 are the signals from cells which have been treated only with the solvent (0.3% DMSO). The values of the preparations treated with test substance are calculated from this as percent of control, and IC50 values are determined by means of RS1.

Description of the Method for the Testing of DNA-PK Inhibitors

The kinase assay is carried out in 348-well microtitre FlashPlates®, coated with streptavidin. 1.5 µg of the DNA-PK protein complex and 100 mg of biotinylated substrate, for example PESQEAFADLWKK biotin-NH2 ("biotin-DNA-PK peptide") in a total volume of 36.5 µl (34.25 mM Hepes/ KOH, 7.85 mM Tris-HCl, 68.5 mM KCl, 5 µM ATP, 6.85 mM MgCl2, 0.5 mM EDTA, 0.14 mM EGTA, 0.69 mM DTT, pH 7.4), are incubated at room temperature for 90 minutes with or without test substance in a well containing 500 ng of DNA from calf thymus, 0.1 µCi of 33P-ATP and 1.8% of DMSO. The reaction is stopped by addition of 50 µl/well of 200 mM EDTA. After incubation for 30 minutes, the liquids are removed at room temperature. Each well is washed three times with 100 µl of 0.9% NaCl solution. Non-specific reaction (blank) is determined using a proprietary kinase inhibitor (10 µM). The radioactivity is measured by means of a Topcount. IC50 values calculated in RS1. Literature: Molecular Cancer Therapeutics 2003, 1257-1264; DNA-dependent protein kinase inhibitors as drug candidates for the treatment of cancer; A. Kashishian, H. Douangpanya, D. Clark, S. T. Schlachter, C. Todd Eary, J. G. Schiro, H. Huang, L. E. Burgess, E. A. Kesicki, and J. Halbrook.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate, evaporated and purified by chromatography on silica gel and/or by crystallisation. Rf values on silica gel; eluent: ethyl acetate/methanol 9:1.

Mass spectrometry (MS): EI (electron impact ionisation) M+

FAB (fast atom bombardment) (M+H)+
ESI (electrospray ionisation) (M+H)+
APCI-MS (atmospheric pressure chemical ionisation-mass spectrometry) (M+H)+.

Abbreviations:
M—mol/l
min.—minute(s)
h—hour(s)
THF—tetrahydrofuran
Me—methyl
MTBE—tert-butyl methyl ether
DMF—N,N-dimethylformamide
EtOAc—ethyl acetate
HOAc—acetic acid
PE—petroleum ether
Et$_2$O—diethyl ether
NBS—N-bromosuccinimide
MeOH—methanol
EtOH—ethanol
TFA—trifluoroacetic acid
Tf—triflate (—SO$_2$—CF$_3$)
TMS—trimethylsilyl
conc. HCl—concentrated hydrochloric acid
Cy—cyclohexyl General Experimental Conditions:

All work with air- or moisture-sensitive substances is carried out under an argon or nitrogen atmosphere. All commercially available reagents and solvents are employed without further purification, unless indicated otherwise.

Thin-Layer Chromatography (TLC):

Merck silica gel 60 F-254 TLC plates (glass or aluminium). The detection is carried out in the UV, using I$_2$ and/or using 5% ethanolic phosphmolybdate solution with subsequent heating by means of a hot-air fan.

Column chromatography:

Stationary phase Merck silica gel 60, 63-200 μm or Merck silica gel 60, 40-63 μm.

Microwave (MW):

Emrys™ Optimiser EXP from Personal Chemistry

Melting Points (m.p.):

The melting-point determination is carried out by means of a Büchi B-5459 melting point apparatus. All melting points indicated are uncorrected.

Nuclear Resonance Spectroscopy (NMR):

$^1$H- and $^{13}$C-NMR spectra are recorded on 300, 400 and 500 MHz NMR instruments from Bruker. The chemical shifts δ are indicated in ppm, the coupling constants in Hz.

RP-HPLC with UV and MS Detection (LC-MS):

$t_R$—retention time; TIC—total ion count, [MH]$^+$ as m/e values; instrument—Aglient 1100 series (DAD and MS detector) with Sedex 75 ELS detector from ERC; ion source—electrospray (positive mode); scan—100-1000 m/e; fragmentation voltage—60 V; gas temperature—300° C.; DAD—220 nm; flow rate—2.4 ml/min, a splitter reduces the flow rate after the DAD for MS detection to 0.75 ml/min.; column—Chromolith Speed ROD RP-18e 50-4.6; solvent—LiChrosolv (Merck KGaA); mobile phase A—H$_2$O (0.01% TFA); mobile phase B—acetonitrile (0.01% TFA); gradient—from 96% A to 100% B in 2.6 min; then 100% B for 0.7 min.

HPLC Conditions N:

N:gradient: 5.5 min; flow rate.: 2.75 ml/min from 90:10 to −0:100 H$_2$O/ACN

Water+TFA (0.01% vol.); acetonitrile+TFA (0.01% vol.)

Column: Chromolith SpeedROD RP 18e 50-4.6

Wavelength: 220 nm

LCMS Polar Method:

Agilent 1200 series instrument

Column: Chromolith Speed Rod RP 18e 50-4.6 mm

LCMS polar.m, 2.4 ml/min, 220 nm, buffer A 0.05% of HCOOH/H$_2$O, buffer B 0.04% of HCOOH/acetonitrile, 0.0-3.0 min 5%-100% of B, 3.0-3.5 min buffer B.

Synthesis sequence 1: ("A1", "A2", "A3")

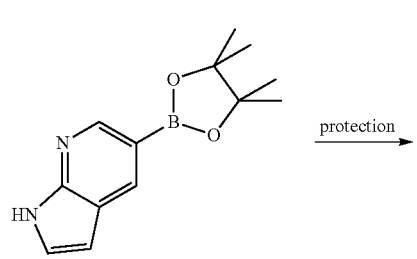

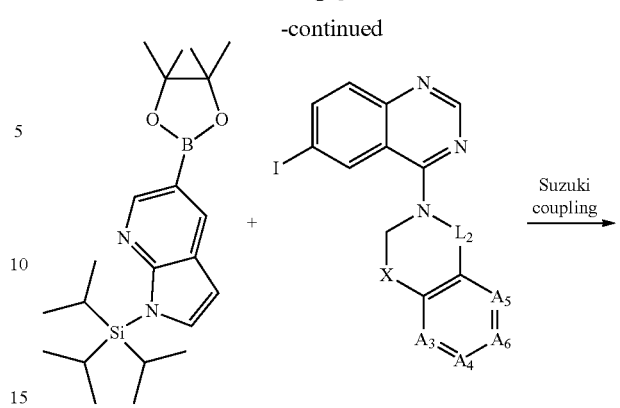

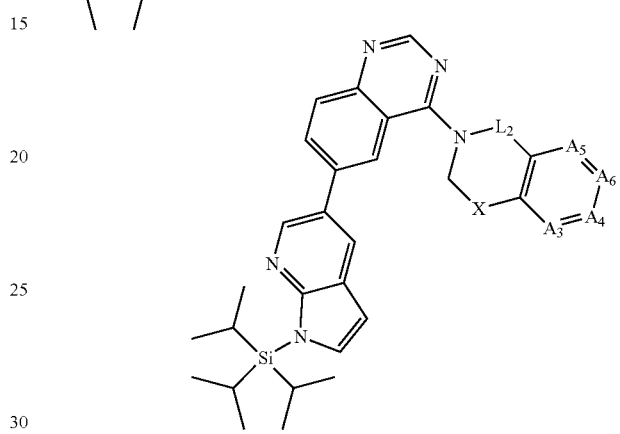

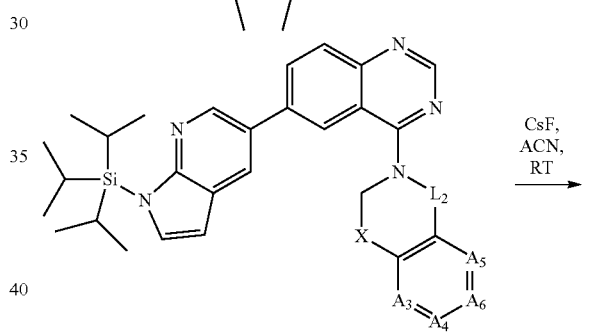

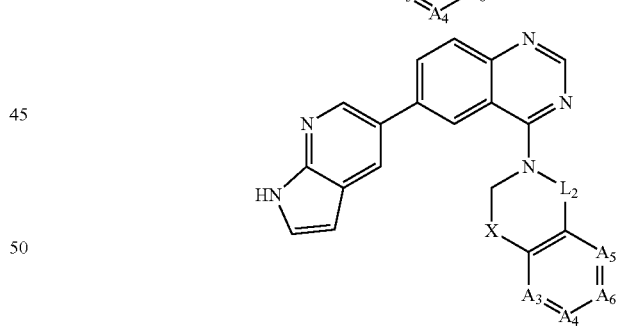

Synthesis sequence 2: ("A4", "A5", "A11", "A12", "A13")

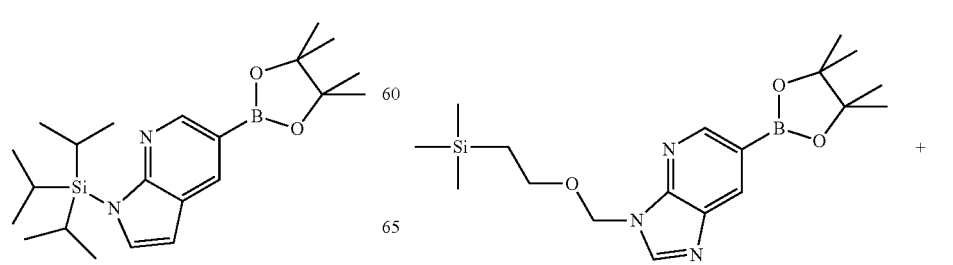

35
-continued
36
-continued
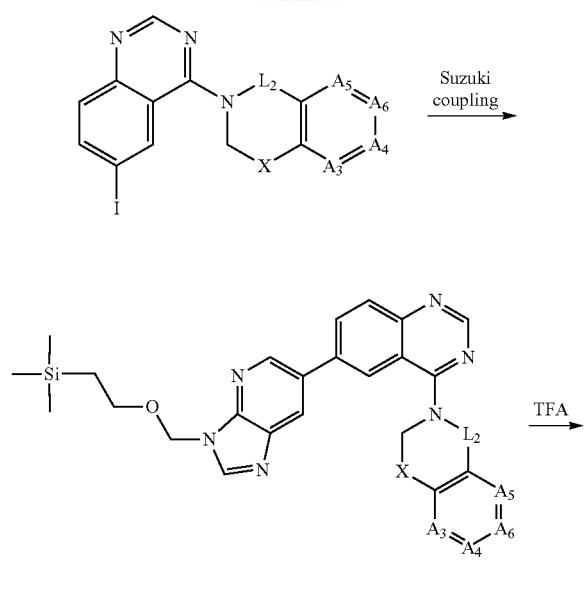
Suzuki coupling
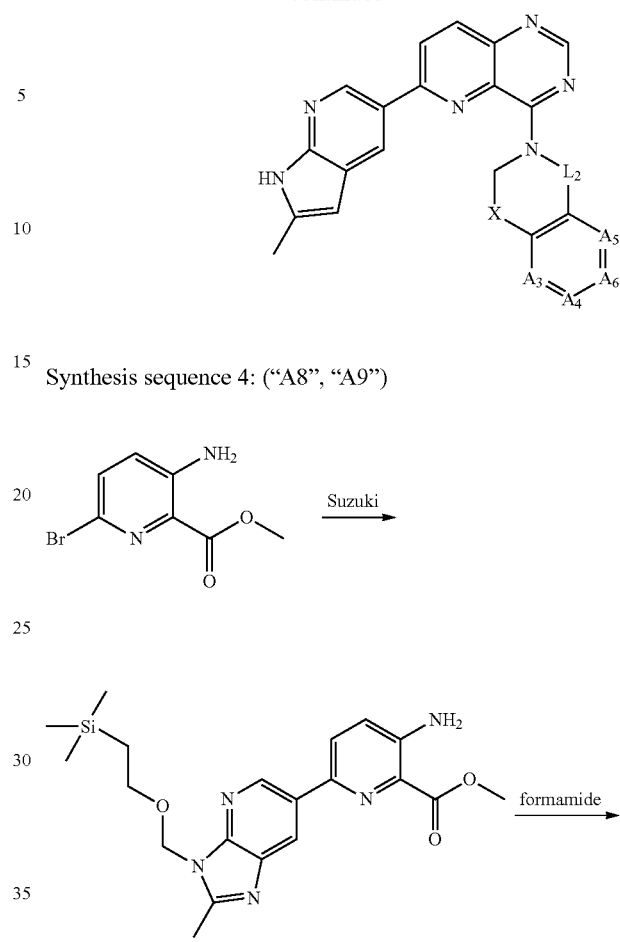
Synthesis sequence 4: ("A8", "A9")
Synthesis sequence 3: ("A6", "A7")
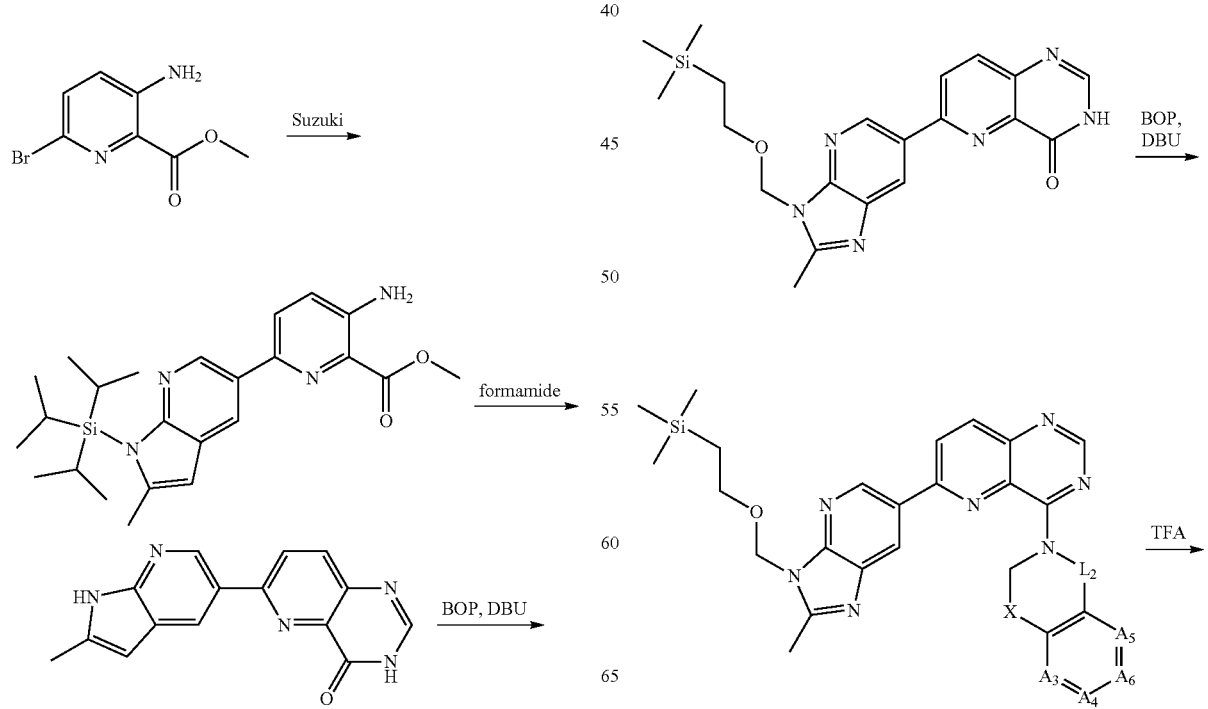

Synthesis sequence 5: ("A10")

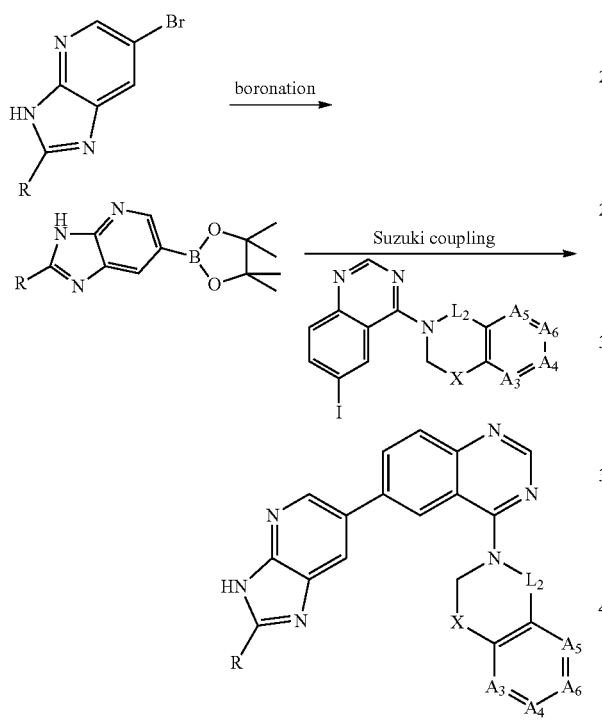

EXAMPLE 1

Preparation of 4-(2,3-dihydroindol-1-yl)-6-(1H-pyrrolo[2,3-b]pyridin-5-yl)-quinazoline ("A1")

1.1 Preparation of 5-(4,4,5,5-tetramethyl-1,3,2-dioxaborolan-2-yl)-1-triisopropylsilanyl-1H-pyrrolo[2,3-b]pyridine

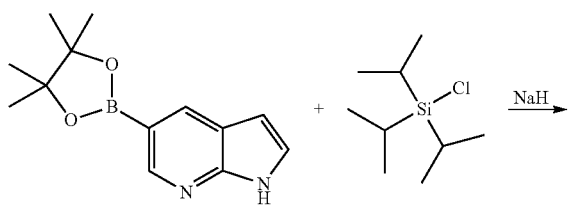

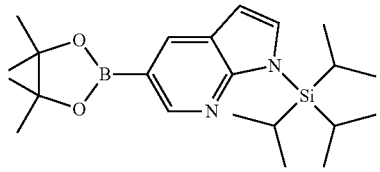

3.00 g of 5-(4,4,5,5-tetramethyl-1,3,2-dioxaborolan-2-yl)-1H-pyrrolo[2,3-b]pyridine are suspended in 40 ml of tetrahydrofuran in a flask. 0.73 g of sodium hydride (60% in paraffin oil) are added in portions with ice-cooling. 3.94 ml of chlorotriisopropylsilane is subsequently added dropwise at about 25° C., and the mixture is heated at 40° C. (bath temperature) under nitrogen until the boronic acid ester has reacted completely (HPLC check, about 5 hours). The excess sodium hydride is deactivated using 10 ml of saturated sodium chloride solution. The solvent is removed in vacuo. The residue is diluted with about 50 ml of water and extracted three times with diethyl ether. The combined organic phases are dried over sodium sulfate and purified by means of column chromatography (gradient heptane: EA 5-100% in 15 min.), giving 4.55 g of 5-(4,4,5,5-tetramethyl-1,3,2-dioxaborolan-2-yl)-1-triisopropylsilanyl-1H-pyrrolo[2,3-b]pyridine as white solid (yield 92%, content 92%); MS-FAB (M+H$^+$)=401.2; R$_f$ (nonpolar method): 3.61 min.

1.2 Preparation of 4-(2,3-dihydroindol-1-yl)-6-iodoquinazoline

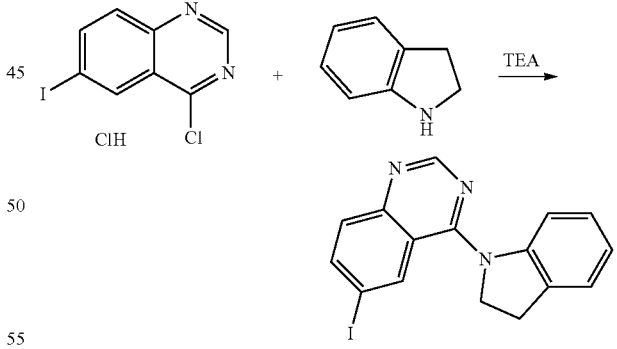

0.60 g of 4-chloro-6-iodoquinazoline, 0.31 ml of 2,3-dihydro-1H-indole and 0.50 ml of triethylamine in 5.00 ml of dioxane are heated at 80° C. in a flask until the quinazoline has reacted completely (HPLC check, about 24 hours). The cooled reaction solution is evaporated to dryness in a rotary evaporator. The residue is purified by means of column chromatography (gradient EA: methanol 0-20% in 16 min.), giving 0.60 g of 4-(2,3-dihydroindol-1-yl)-6-iodoquinazoline as yellowish solid (yield 85%, content 97%); MS-FAB (M+H$^+$)=373.8; R$_f$(polar method): 2.21 min.

1.3 Preparation of 4-(2,3-dihydroindol-1-yl)-6-(1-triisopropylsilanyl-1H-pyrrolo-[2,3-b]pyridin-5-yl) quinazoline

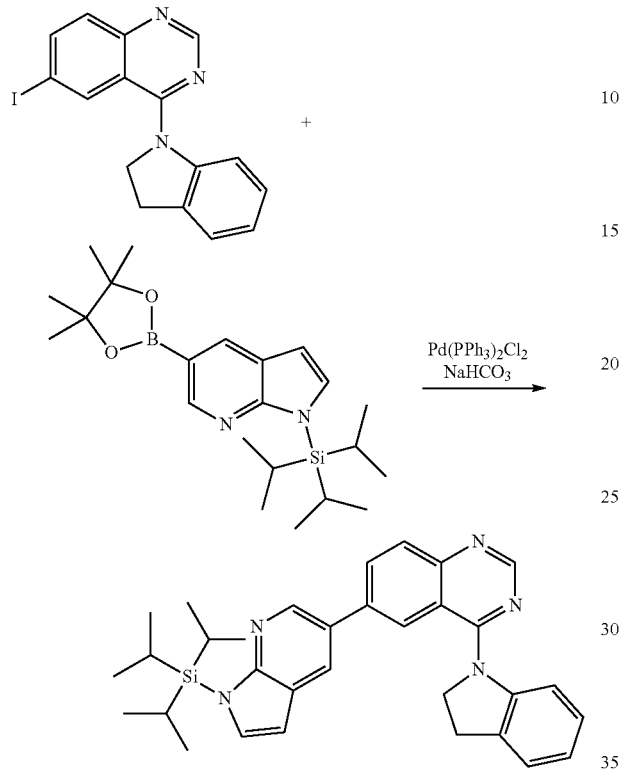

0.20 g of 4-(2,3-dihydroindol-1-yl)-6-iodoquinazoline, 0.21 g of 5-(4,4,5,5-tetramethyl-1,3,2-dioxaborolan-2-yl)-1-triisopropylsilanyl-1H-pyrrolo[2,3-b]pyridine, 0.13 g of sodium hydrogencarbonate and 0.07 g of Pd(PPh$_3$)$_2$Cl$_2$ in 5.00 ml of dioxane and 0.50 ml of water are heated at 90° C. under nitrogen in a flask until the reaction is complete (HPLC check, about 5 hours). The cooled reaction solution is diluted with EA and washed 3 times with water. The organic phase is dried over sodium sulfate and purified by means of column chromatography; (gradient heptane: EA 5-100% in 16 min), giving 0.20 g of 4-(2,3-dihydroindol-1-yl)-6-(1-triisopropylsilanyl-1H-pyrrolo[2,3-b]pyridin-5-yl)-quinazoline as white powder (yield 71%, content 99%); EI-MS (M+H$^+$)=519.2.

1.4 Preparation of 4-(2,3-dihydroindol-1-yl)-6-(1H-pyrrolo[2,3-b]pyridin-5-yl)quinazoline ("A1")

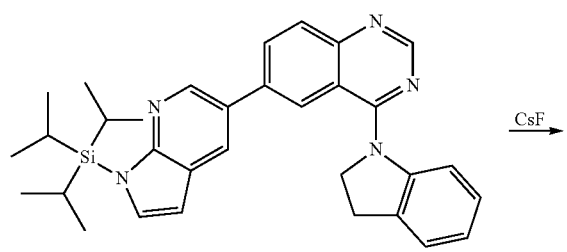

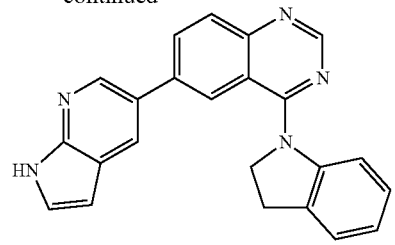

0.19 g of 4-(2,3-dihydroindol-1-yl)-6-(1-triisopropylsilanyl-1H-pyrrolo[2,3-b]-pyridin-5-yl)quinazoline and 0.08 g of caesium fluoride in 1 ml of acetonitrile are stirred at 25° C. in a flask until the reaction is complete (HPLC check, about 24 hours). A precipitate precipitates out of the reaction solution. This is filtered off, rinsed with water and dried, giving 0.04 g of 4-(2,3-dihydroindol-1-yl)-6-(1H-pyrrolo[2,3-b]pyridin-5-yl)quinazoline as white solid (yield 31%, content 97%); MS-FAB (M+H$^+$)=363.9; R$_f$ (polar method): 1.71 min; $^1$H NMR (500 MHz, DMSO-d$_6$) δ [ppm] 11.76 (s, 1H), 8.74 (s, 1H), 8.58 (d, J=2.1, 1H), 8.32 (dd, J=13.7, 1.9, 2H), 8.27 (dd, J=8.7, 1.9, 1H), 7.98 (d, J=8.7, 1H), 7.54 (d, J=3.2, 1H), 7.49 (d, J=8.0, 1H), 7.35 (d, J=7.2, 1H), 7.17 (t, J=7.6, 1H), 7.01 (t, J=7.3, 1H), 6.52 (d, J=3.3, 1H), 4.56 (t, J=8.0, 2H), 3.22 (t, J=7.9, 2H).

EXAMPLE 2

Preparation of 4-(1,3-dihydroisoindol-2-yl)-6-(1H-pyrrolo[2,3-b]pyridin-5-yl)-quinazoline ("A2")

2.1 Preparation of 4-(1,3-dihydroisoindol-2-yl)-6-iodoquinazoline

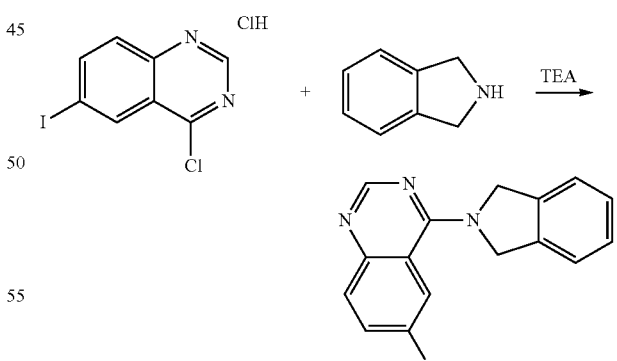

0.50 g of 4-chloro-6-iodoquinazoline, 0.27 g of 2,3-dihydro-1H-isoindole, 0.42 ml of triethylamine in 4 ml of dioxane are heated at 80° C. in a flask until the quinazoline has reacted virtually completely (HPLC check, about 3 hours). The cooled reaction solution is evaporated to dryness in a rotary evaporator. The residue is suspended in EA. The undissolved solid is filtered off, rinsed with water and dried, giving 0.56 g of 4-(1,3-dihydroisoindol-2-yl)-6-iodoquinazoline as slightly yellowish solid (yield 93%, content 94%); MS-FAB (M+H$^+$)=373.8; R$_f$ (polar method): 1.73 min. This is employed for the next step without further purification.

2.2 Preparation of 4-(1,3-dihydroisoindol-2-yl)-6-(1-triisopropylsilanyl-1H-pyrrolo[2,3-b]pyridin-5-yl)quinazoline

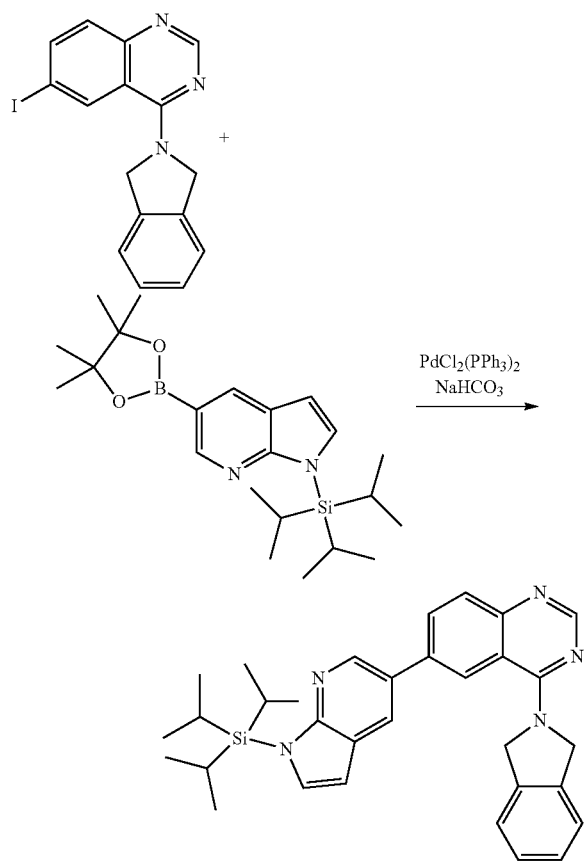

0.25 g of 4-(1,3-dihydroisoindol-2-yl)-6-iodoquinazoline, 0.32 g of 5-(4,4,5,5-tetramethyl-1,3,2-dioxaborolan-2-yl)-1-triisopropylsilanyl-1H-pyrrolo[2,3-b]-pyridine, 0.16 g of sodium hydrogencarbonate and 0.09 g of PdCl$_2$(PPh$_3$)$_2$ in 5.00 ml of dioxane and 0.50 ml of water are heated at 90° C. under nitrogen in a flask until the iodide has reacted completely (HPLC check, about 8 hours). The cooled reaction solution is diluted with EA and washed 3 times with water. The organic phase is dried over sodium sulfate and purified by means of column chromatography (gradient heptane: EA 5-100% in 30 min), giving 0.12 g of 4-(1,3-dihydroisoindol-2-yl)-6-(1-triisopropylsilanyl-1H-pyrrolo[2,3-b]pyridin-5-yl)quinazoline as slightly beige solid (yield 33%, content 95%); MS-FAB (M+H$^+$)=520.0; R$_f$(polar method): 2.77 min.

2.3 Preparation of 4-(1,3-dihydroisoindol-2-yl)-6-(1H-pyrrolo[2,3-b]pyridin-5-yl)quinazoline

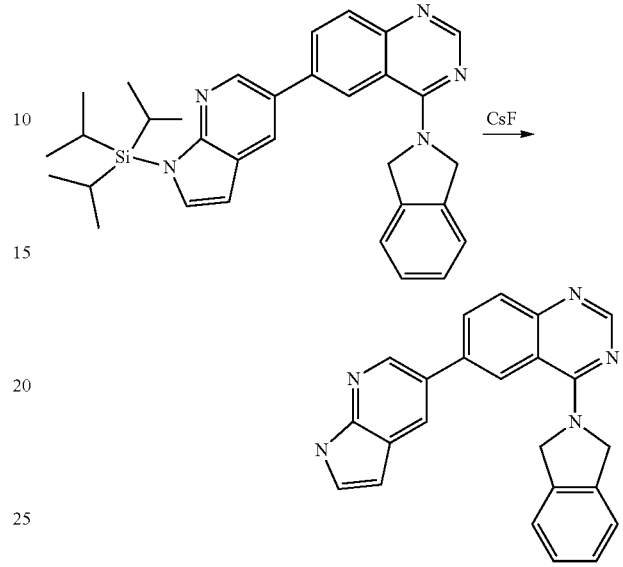

0.12 g of 4-(1,3-dihydroisoindol-2-yl)-6-(1-triisopropylsilanyl-1H-pyrrolo[2,3-b]-pyridin-5-yl)quinazoline and 0.05 g of caesium fluoride in 1 ml of acetonitrile are stirred at 25° C. in a flask until the reaction is complete (HPLC check about 24 hours). A precipitate precipitates out of the reaction solution. This is filtered off, rinsed with water and dried, giving 0.08 g of 4-(1,3-dihydroisoindol-2-yl)-6-(1H-pyrrolo[2,3-b]pyridin-5-yl)quinazoline ("A2") as white solid (yield 95%, content 96%); MS-FAB (M+H$^+$)=363.8; R$_f$(polar method): 1.63 min;

$^1$H NMR (500 MHz, DMSO-d$_6$) δ [ppm] 11.76 (s, 1H), 8.72 (d, J=2.2, 2H), 8.56 (s, 1H), 8.41 (d, J=2.0, 1H), 8.17 (dd, J=8.6, 1.8, 1H), 7.87 (d, J=8.6, 1H), 7.57-7.54 (m, 1H), 7.51 (dd, J=5.4, 3.2, 2H), 7.36 (dd, J=5.6, 3.1, 2H), 6.57 (dd, J=3.4, 1.8, 1H), 5.48 (d, J=33.1, 2H), 1.04 (d, J=2.6, 2H).

EXAMPLE 3

Preparation of 4-(3,4-dihydro-2H-quinolin-1-yl)-6-(1H-pyrrolo[2,3-b]pyridin-5-yl)quinazoline ("A3")

3.1 Preparation of 4-(3,4-dihydro-2H-quinolin-1-yl)-6-(1H-pyrrolo-[2,3-b]pyridin-5-yl)quinazoline

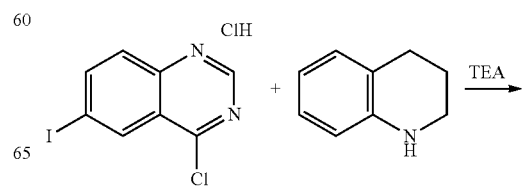

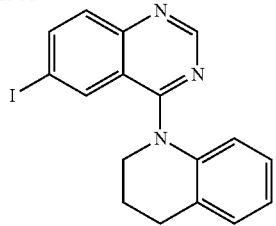

0.50 g of 4-chloro-6-iodoquinazoline, 0.30 g of 1,2,3,4-tetrahydroquinoline and 0.40 ml of triethylamine in 4 ml of dioxane are heated at 80° C. in a flask until the quinazoline has reacted completely (HPLC check, about 24 hours). The cooled reaction solution is evaporated to dryness in a rotary evaporator. The residue is purified by means of column chromatography (gradient heptane: EA 5-100% in 16 min.), giving 0.27 g of 4-(3,4-dihydro-2H-quinolin-1-yl)-6-(1H-pyrrolo[2,3-b]pyridin-5-yl)quinazoline as yellow solid (yield 43%, content 96%); MS-FAB (M+H$^+$)=387.8; R$_f$ (polar method): 2.43 min.

3.2 Preparation of 4-(3,4-dihydro-2H-quinolin-1-yl)-6-(1-triisopropylsilanyl-1H-pyrrolo[2,3-b]pyridin-5-yl)quinazoline

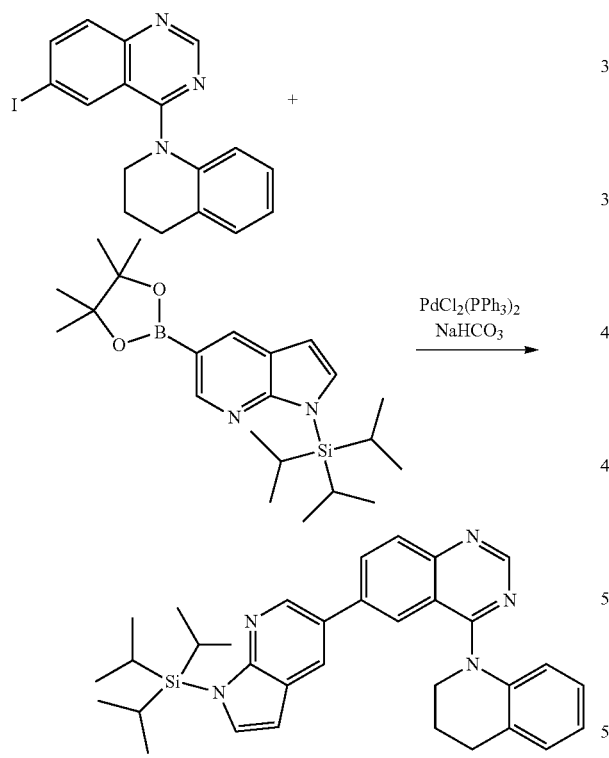

0.25 g of 4-(3,4-dihydro-2H-quinolin-1-yl)-6-(1H-pyrrolo[2,3-b]pyridin-5-yl)-quinazoline, 0.31 g of 5-(4,4,5,5-tetramethyl-1,3,2-dioxaborolan-2-yl)-1-triisopropylsilanyl-1H-pyrrolo[2,3-b]pyridine, 0.16 g of sodium hydrogencarbonate and 90 mg of PdCl$_2$(PPh$_3$)$_2$ in 5.00 ml of dioxane and 0.50 ml of water are heated at 90° C. under nitrogen in a flask until the reaction is complete (HPLC check, about 18 hours). The cooled reaction solution is diluted with EA and washed 3 times with water. The organic phase is dried over sodium sulfate and purified by means of column chromatography (gradient heptane: EA 5-100% in 16 min), giving 0.20 g of 4-(3,4-dihydro-2H-quinolin-1-yl)-6-(1-triisopropylsilanyl-1H-pyrrolo[2,3-b]pyridin-5-yl)-quinazoline as yellow oil (yield 50%, content 83%).

This is employed for the next step without further purification.

3.3 Preparation of 4-(3,4-dihydro-2H-quinolin-1-yl)-6-(1H-pyrrolo-[2,3-b]pyridin-5-yl)quinazoline

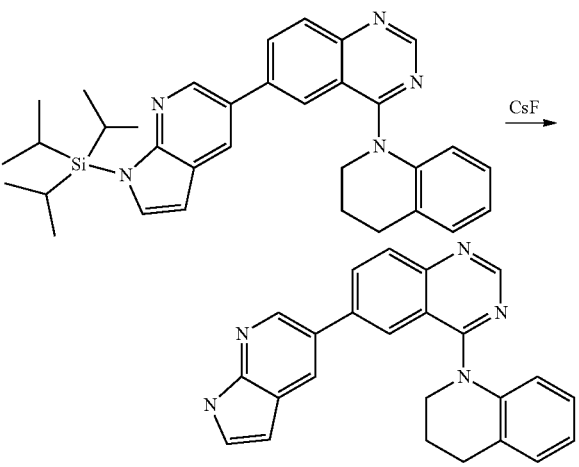

0.20 g of 4-(3,4-dihydro-2H-quinolin-1-yl)-6-(1-triisopropylsilanyl-1H-pyrrolo[2,3-b]pyridin-5-yl)quinazoline and 0.08 g of caesium fluoride in 1 ml of acetonitrile and 1 ml of dichloromethane are stirred at 25° C. in a flask until the reaction is complete (HPLC check, about 24 hours). A precipitate precipitates out of the reaction solution. This is filtered off, rinsed with water and dried, giving 0.02 g of 4-(3,4-dihydro-2H-quinolin-1-yl)-6-(1H-pyrrolo[2,3-b]pyridin-5-yl)quinazoline ("A3") as white solid (yield 13%, content 95%); MS-FAB (M+H$^+$)=377.9; R$_f$ (polar method): 1.79 min; $^1$H NMR (500 MHz, DMSO-d$_6$) δ [ppm] 11.70 (s, 1H), 8.85 (s, 1H), 8.15 (dd, J=8.7, 2.0, 1H), 8.11 (d, J=2.1, 1H), 7.94 (d, J=8.7, 1H), 7.87 (d, J=2.0, 1H), 7.58 (d, J=1.9, 1H), 7.54-7.48 (m, 1H), 7.35 (d, J=7.0, 1H), 7.14 (t, J=7.0, 1H), 7.07 (t, J=7.5, 1H), 6.77 (d, J=7.9, 1H), 6.44 (dd, J=3.3, 1.8, 1H), 4.05 (t, J=6.5, 2H), 2.89 (t, J=6.5, 2H), 2.12-2.00 (m, 2H).

EXAMPLE 4

Preparation of 4-(3,4-dihydro-1H-isoquinolin-2-yl)-6-(1H-pyrrolo[2,3-b]pyridin-5-yl)pyrido[3,2-d]pyrimidine ("A6")

4.1 Preparation of methyl 3-amino-6-bromopyridine-2-carboxylate

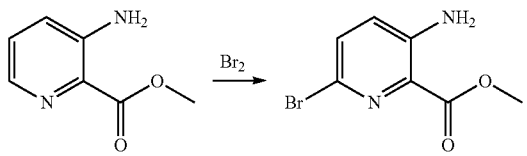

20 g of methyl 3-aminopyridine-2-carboxylate are suspended in 120 ml of water in a flask. After addition of 100 ml of sulfuric acid (2 mol/l), the mixture is cooled to 0° C., 6.73 ml of bromine are added dropwise, and the mixture is stirred at 25° C. until the acid has reacted completely (HPLC check, about 24 hours). A precipitate precipitates out of the reaction solution. This is filtered off, dissolved in EA, washed with sodium thiosulfate solution, the organic phase is dried and purified by means of column chromatography (gradient heptane: EA 5-100% in 30 min.), giving 15 g of methyl 3-amino-6-bromo-pyridine-2-carboxylate as red-brown solid (yield 50%, content 98%); MS-FAB (M+H⁺)=232.9; R$_f$ (polar method): 1.518 min.

4.2 Preparation of methyl 3-amino-6-(1-triisopropyl-silanyl-1H-pyrrolo-[2,3-b]pyridin-5-yl)pyridine-2-carboxylate

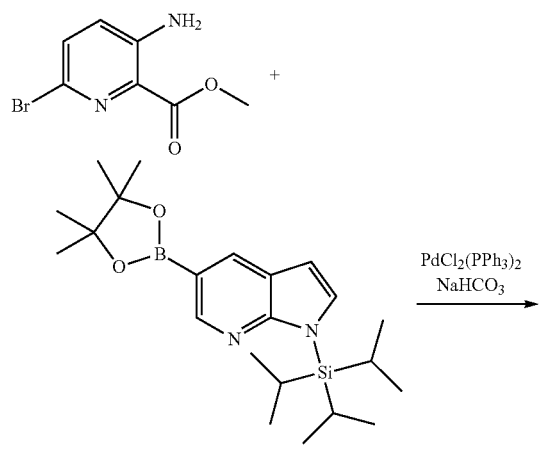

7.50 g of methyl 3-amino-6-bromopyridine-2-carboxylate, 12.10 g of 5-(4,4,5,5-tetramethyl-1,3,2-dioxaborolan-2-yl)-1-triisopropylsilanyl-1H-pyrrolo-[2,3-b]pyridine, 8.18 g of sodium hydrogencarbonate and 2.27 g of PdCl$_2$(PPh$_3$)$_2$ in 90 ml of dioxane and 15 ml of water are heated at 90° C. under nitrogen in a flask until the reaction is complete (HPLC check, about 7 hours). The cooled reaction solution is diluted with EA and washed 3 times with water. The organic phase is dried over sodium sulfate and purified by means of column chromatography (gradient heptane: EA 5-100% in 25 min), giving 8.40 g of methyl 3-amino-6-(1-triisopropylsilanyl-1H-pyrrolo[2,3-b]pyridin-5-yl)pyridine-2-carboxylate as white solid (yield 56%, content 92%); MS-FAB (M+H⁺)=425.2; R$_f$ (Esi1rod method): 3.10 min.

4.3 Preparation of 6-(1H-pyrrolo[2,3-b]pyridin-5-yl)-3H-pyrido[3,2-d]-pyrimidin-4-one

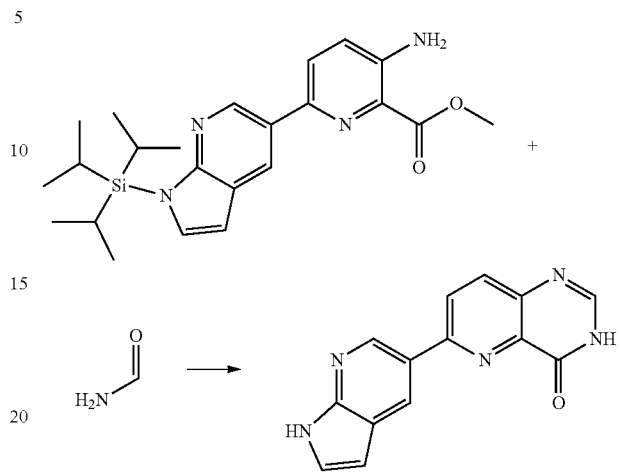

3.80 g of methyl 3-amino-6-(1-triisopropylsilanyl-1H-pyrrolo[2,3-b]pyridin-5-yl)-pyridine-2-carboxylate in 60 ml of formamide are heated at 120° C. under nitrogen in a flask until the reaction is complete (HPLC check, about 52 hours). The cooled reaction solution is added to about 50 ml of water, during which a precipitate precipitates out. This is filtered off with suction and dried, giving 2.00 g of 6-(1H-pyrrolo[2,3-b]pyridin-5-yl)-3H-pyrido[3,2-d]pyrimidin-4-one as orange solid (yield 83%, content 98%); MS-FAB (M+H⁺)=264.1; R$_f$ (polar method): 1.28 min.

This is employed for the next step without further purification.

4.4 Preparation of 4-(3,4-dihydro-1H-isoquinolin-2-yl)-6-(1H-pyrrolo[2,3-b]-pyridin-5-yl)pyrido[3,2-d]pyrimidine

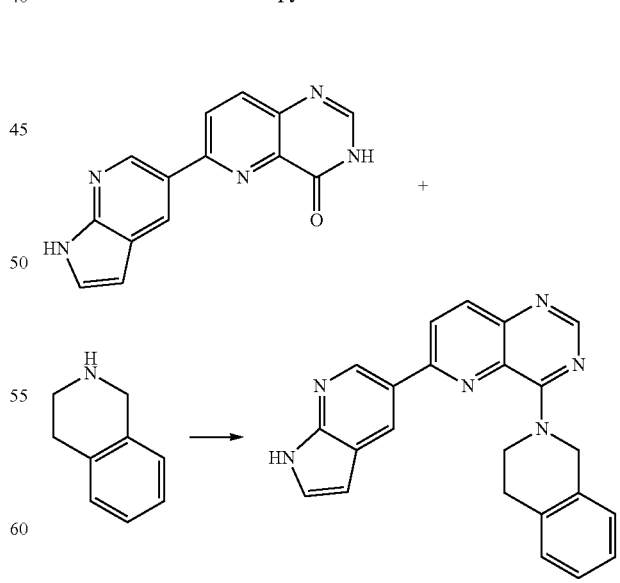

0.20 g of 6-(1H-pyrrolo[2,3-b]pyridin-5-yl)-3H-pyrido[3,2-d]pyrimidin-4-one and 139 µl of 1,2,3,4-tetrahydroisoquinoline are suspended in 10 ml of acetonitrile and 1 ml of dimethylformamide in a flask. 0.65 g of (benzotriazol-1- yloxy)tris-(dimethylamino)phosphonium hexafluorophosphate, 255 µl of 1,8-diaza-bicyclo[5.4.0]undec-7-ene are subsequently added, and the mixture is heated at 60° C. under nitrogen until the reaction has proceeded to completion (HPLC check, about 5 hours). A precipitate precipitates out of the reaction solution. This is filtered off, rinsed with water and dried, giving 0.20 g of 4-(3,4-dihydro-1H-isoquinolin-2-yl)-6-(1H-pyrrolo[2,3-b]pyridin-5-yl)pyrido[3,2-d]pyrimidine ("A6") as white solid (yield 65%, content 94%); MS-FAB (M+H$^+$)=379.1; R$_f$ (polar method): 1.86 min;

$^1$H NMR (500 MHz, DMSO-d$_6$) δ [ppm] 11.87 (s, 1H), 9.10 (d, J=2.0, 1H), 8.75 (d, J=1.8, 1H), 8.56 (s, 1H), 8.49 (d, J=8.9, 1H), 8.20 (d, J=8.9, 1H), 7.61-7.56 (m, 1H), 7.32-7.18 (m, 4H), 6.63 (dd, J=3.3, 1.7, 1H), 4.69 (s, 3H), 3.16 (s, 2H), 2.07 (s, 1H).

EXAMPLE 5

Preparation of 4-(6,7-dimethoxy-3,4-dihydro-1H-isoquinolin-2-yl)-6-(1H-pyrrolo[2,3-b]pyridin-5-yl)pyrido[3,2-d]pyrimidine ("A7")

Preparation of 4-(6,7-dimethoxy-3,4-dihydro-1H-isoquinolin-2-yl)-6-(1H-pyrrolo[2,3-b]pyridin-5-yl)pyrido[3,2-d]pyrimidine

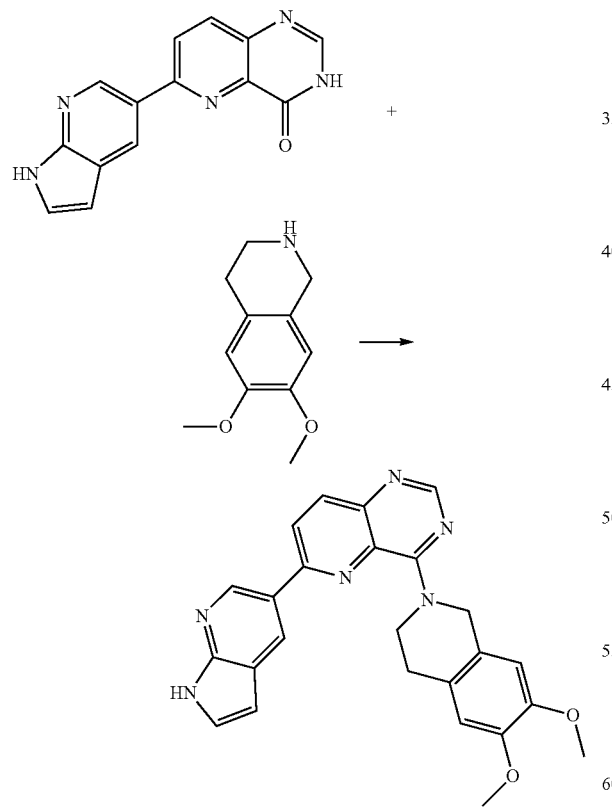

0.20 g of 6-(1H-pyrrolo[2,3-b]pyridin-5-yl)-3H-pyrido[3,2-d]pyrimidin-4-one and 0.22 g of 6,7-dimethoxy-1,2,3,4-tetrahydroisoquinoline are suspended in 10 ml of acetonitrile and 1 ml of dimethylformamide in a flask. 0.65 g of (benzotriazol-1-yloxy)tris-(dimethylamino)phosphonium hexafluorophosphate, 255 µl of 1,8-diazabicyclo[5.4.0]undec-7-ene are subsequently added, and the mixture is heated at 60° C. under nitrogen until the reaction has proceeded to completion (HPLC check, about 5 hours). A precipitate precipitates out of the reaction solution. This is filtered off, rinsed with water and dried, giving 0.17 g of 4-(6,7-dimethoxy-3,4-dihydro-1H-isoquinolin-2-yl)-6-(1H-pyrrolo[2,3-b]pyridin-5-yl)pyrido[3,2-d]pyrimidine ("A7") as white solid (yield 50%, content 97%); MS-FAB (M+H$^+$)=439; R$_f$ (polar method): 1.68 min;

$^1$H NMR (500 MHz, DMSO-d$_6$) δ [ppm] 11.87 (s, 1H), 9.10 (d, J=1.9, 1H), 8.75 (d, J=1.7, 1H), 8.55 (s, 1H), 8.49 (d, J=8.9, 1H), 8.19 (d, J=8.8.1H), 7.61-7.55 (m, 1H), 6.89 (s, 1H), 6.85 (s, 1H), 6.61 (dd, J=3.3, 1.8, 1H), 3.75 (d, J=6.8, 6H), 3.08 (s, 2H), 2.84-2.70 (m, 2H), 2.66 (dd, J=26.0, 24.3, 2H).

EXAMPLE 6

Preparation of 4-(3,4-dihydro-1H-isoquinolin-2-yl)-6-(2-methyl-3H-imidazo-[4,5-b]pyridin-6-yl)quinazoline ("A4")

6.1 Preparation of 6-bromo-2-methyl-1-(2-trimethylsilanylethoxymethyl)-1H-imidazo[4,5-b]pyridine 8.00 g of 6-bromo-2-methyl-3H-imidazo[4,5-b]pyridine in 275 ml of tetrahydrofuran is initially introduced in a flask. 1.66 g of sodium hydride (60% in paraffin oil) are added in portions with ice-cooling. 7.00 ml of 2-trimethylsilylethoxymethyl chloride is subsequently added dropwise at about −30° C., and the mixture is stirred at 25° C. under nitrogen until the pyridine has reacted completely (HPLC check, about 4 hours). The cooled reaction solution is added to about 200 ml of water and extracted three times with EA. The combined organic phases are dried over sodium sulfate and purified by means of column chromatography (gradient heptane: EA 5-100% in 34 min.), giving 5.30 g of 6-bromo-2-methyl-1-(2-trimethylsilanylethoxymethyl)-1H-imidazo[4,5-b]pyridine as white solid (yield 40%, content 99%); MS-FAB (M+H$^+$)=343.1; R$_f$ (polar method): 2.59 min.

6.2 Preparation of 2-methyl-6-(4,4,5,5-tetramethyl-1,3,2-dioxaborolan-2-yl)-3-(2-trimethylsilanylethoxymethyl)-3H-imidazo[4,5-b]pyridine

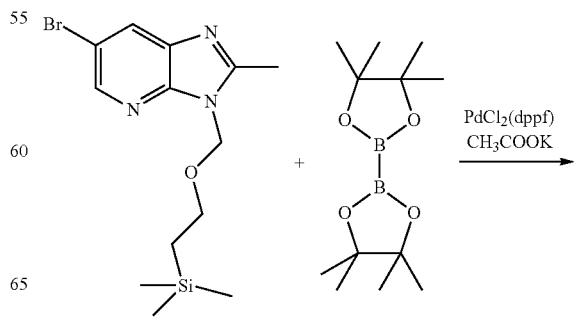

-continued

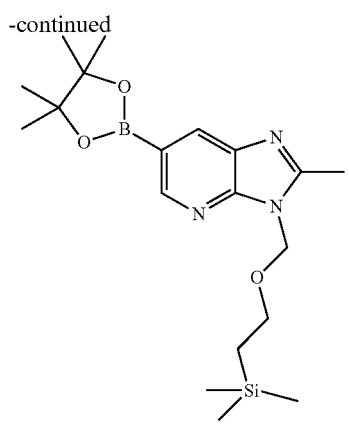

4.00 g of 6-bromo-2-methyl-3-(2-trimethylsilanylethoxymethyl)-3H-imidazo-[4,5-b]pyridine, 4.45 g of bis(pinacolato)diboron, 3.44 g of potassium acetate and 1.71 g of PdCl$_2$(dppf) in 35 ml of dimethyl sulfoxide are heated at 90° C. under nitrogen in a flask until the reaction is complete (HPLC check, about 2 hours). The cooled reaction solution is diluted with EA and washed 3 times with water. The organic phase is dried over sodium sulfate and purified by means of column filtration (eluent: EA), giving 3.40 g of 2-methyl-6-(4,4,5,5-tetramethyl-1,3,2-dioxaborolan-2-yl)-3-(2-trimethylsilanylethoxymethyl)-3H-imidazo[4,5-b]pyridine as dark-brown solid (yield 68%, content 92%); MS-FAB (M+H$^+$)=390.2; R$_f$(polar method): 2.69 min.

This is employed for the next step without further purification.

6.3 Preparation of 4-(3,4-dihydro-1H-isoquinolin-2-yl)-6-iodoquinazoline

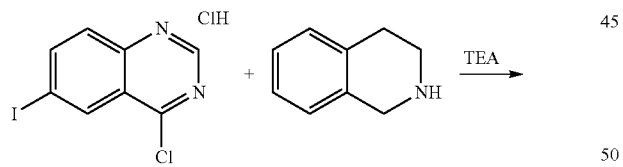

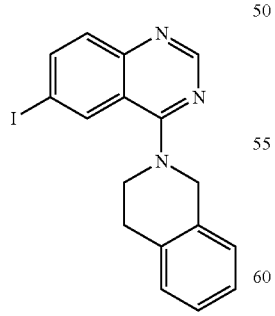

0.75 g of 4-chloro-6-iodoquinazoline, 0.45 g of 1,2,3,4-tetrahydroisoquinoline and 0.63 ml of triethylamine in 6.0 ml of dioxane are heated at 80° C. in a flask until the quinazoline has reacted completely (HPLC check, about 3 hours). The cooled reaction solution is evaporated to dryness in a rotary evaporator. The residue is purified by means of column chromatography (gradient heptane: EA 10-100% in 20 min.), giving 0.87 g of 4-(3,4-dihydro-1H-isoquinolin-2-yl)-6-iodoquinazoline as yellowish solid (yield 90%, content 92%); MS-FAB (M+H$^+$)=388.0; R$_f$(polar method): 1.84 min.

6.4 Preparation of 4-(3,4-dihydro-1H-isoquinolin-2-yl)-6-[2-methyl-3-(2-trimethylsilanylethoxymethyl)-3H-imidazo[4,5-b]pyridin-6-yl]quinazoline

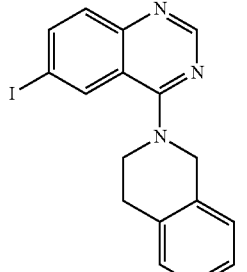

+

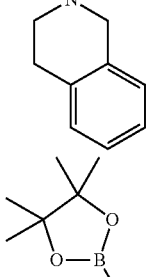

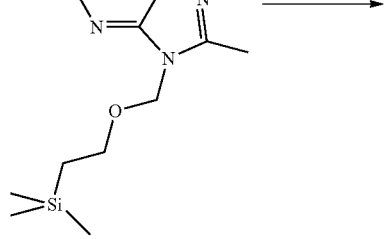

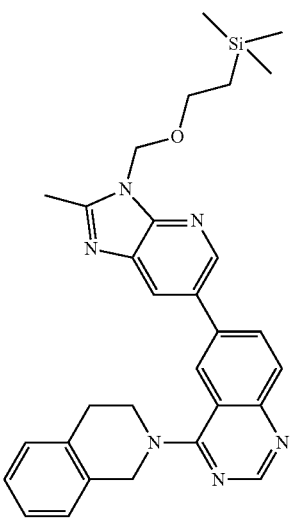

0.87 g of 4-(3,4-dihydro-1H-isoquinolin-2-yl)-6-iodoquinazoline, 0.96 g of 2-methyl-6-(4,4,5,5-tetramethyl-1,3,2-dioxaborolan-2-yl)-3-(2-trimethylsilanylethoxymethyl)-3H-imidazo[4,5-b]pyridine, 0.52 g of sodium hydrogencarbonate and 0.29 g of Pd(PPh$_3$)$_2$Cl$_2$ in 17 ml of dioxane and 2 ml of water are heated at 90° C. under nitrogen in a flask until the reaction is complete (HPLC check, about 3 hours). The cooled reaction solution is diluted with EA and washed 3 times with water. The organic phase is dried over sodium sulfate and purified by means of column chromatography (gradient EA: methanol 0-30% in 20 min), giving 0.85 g of 4-(3,4-dihydro-1H-isoquinolin-2-yl)-6-[2-methyl-3-(2-trimethylsilanylethoxymethyl)-3H-imidazo[4,5-b]pyridin-6-yl]quinazoline as white powder (yield 60%, content 86%); MS-FAB (M+H$^+$)=523.2; R$_f$(polar method): 2.12 min.

6.5 Preparation of 4-(3,4-dihydro-1H-isoquinolin-2-yl)-6-(2-methyl-3H-imidazo[4,5-b]pyridin-6-yl)quinazoline

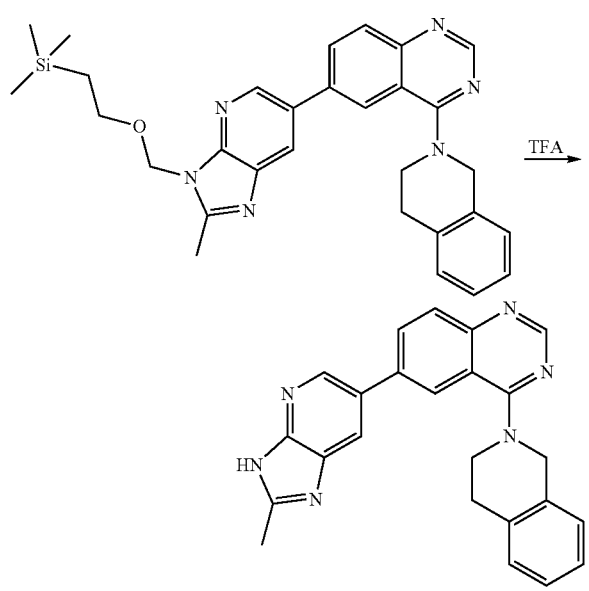

0.70 g of 4-(3,4-dihydro-1H-isoquinolin-2-yl)-6-[2-methyl-3-(2-trimethylsilanylethoxymethyl)-3H-imidazo[4,5-b]pyridin-6-yl]quinazoline and 825 µl of trifluoroacetic acid in 8 ml of dichloromethane are stirred at 25° C. in a flask until the reaction is complete (HPLC check, about 120 hours). The cooled reaction solution is diluted with dichloromethane and washed with sodium hydrogencarbonate solution. The organic phase is dried over sodium sulfate and purified by means of column chromatography (gradient EA: methanol 0-30% in 13 min), giving 0.19 g of 4-(3,4-dihydro-1H-isoquinolin-2-yl)-6-(2-methyl-3H-imidazo[4,5-b]pyridin-6-yl)quinazoline ("A4") as white solid (yield 36%, content 97%); MS-FAB (M+H$^+$)=393.1; R$_f$(polar method): 1.39 min;

$^1$H NMR (500 MHz, DMSO-d$_6$) δ [ppm] 8.64 (s, 1H), 8.29 (d, J=1.8, 2H), 8.22 (dd, J=8.7, 1.9, 2H), 7.91 (d, J=8.7, 1H), 7.36-7.18 (m, 4H), 5.75 (s, 1H), 5.01 (s, 2H), 4.11 (t, J=5.8, 2H), 3.18-3.08 (m, 2H), 2.56 (s, 3H).

EXAMPLE 7

Preparation of 4-(3,4-dihydro-2H-quinolin-1-yl)-6-(2-methyl-3H-imidazo[4,5-b]-pyridin-6-yl)quinazoline ("A5")

7.1 Preparation of 4-(3,4-dihydro-2H-quinolin-1-yl)-6-iodoquinazoline 1.30 g of 4-chloro-6-iodoquinazoline, 1.50 ml of 1,2,3,4-tetrahydroquinoline in 10 ml of dioxane are heated at 110° C. in a flask until the quinazoline has reacted completely (HPLC check, about 3 hours). The cooled reaction solution is diluted with EA and washed 3 times with 5% citric acid. The organic phase is dried over sodium sulfate and purified by means of column chromatography (gradient heptane: EA 0-100% in 18 min.), giving 1.27 g of 4-(3,4-dihydro-2H-quinolin-1-yl)-6-iodoquinazoline as yellowish solid (yield 81%, content 99%); MS-FAB (M+H$^+$)=388.0; R$_f$(polar method): 2.89 min.

7.2 Preparation of 4-(3,4-dihydro-2H-quinolin-1-yl)-6-[2-methyl-3-(2-trimethylsilanylethoxymethyl)-3H-imidazo[4,5-b]pyridin-6-yl]quinazoline

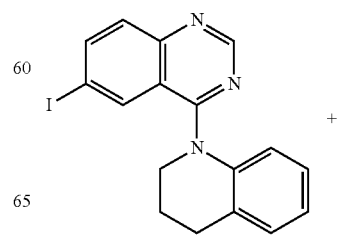

-continued

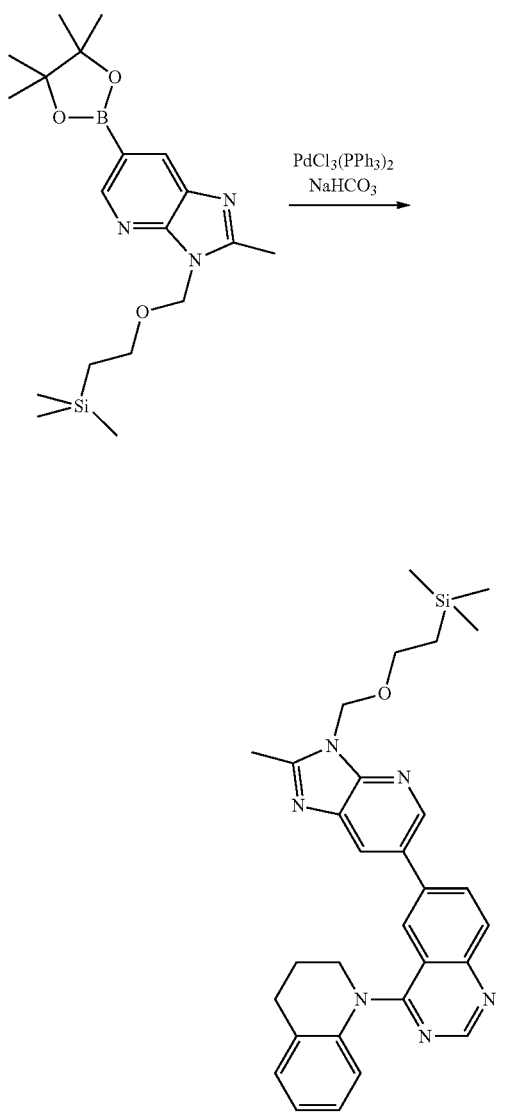

0.25 g of 4-(3,4-dihydro-2H-quinolin-1-yl)-6-iodoquinazoline, 0.30 g of 2-methyl-6-(4,4,5,5-tetramethyl-1,3,2-dioxaborolan-2-yl)-3-(2-trimethylsilanylethoxymethyl)-3H-imidazo[4,5-b]pyridine, 0.16 g of sodium hydrogencarbonate and 0.09 g of Pd(PPh$_3$)$_2$Cl$_2$ in 5.00 ml of dioxane and 0.50 ml of water are heated at 90° C. under nitrogen in a flask until the reaction is complete (HPLC check, about 5 hours). The cooled reaction solution is diluted with EA and washed 3 times with water. The organic phase is dried over sodium sulfate and purified by means of column chromatography (gradient EA: methanol 0-40% in 20 min), giving 0.19 g of 4-(3,4-dihydro-2H-quinolin-1-yl)-6-[2-methyl-3-(2-trimethylsilanylethoxymethyl)-3H-imidazo[4,5-b]pyridin-6-yl]quinazoline as white powder (yield 50%, content 94%); MS-FAB (M+H$^+$)=523.2; R$_f$ (polar method): 2.54 min.

7.3 Preparation of 4-(3,4-dihydro-2H-quinolin-1-yl)-6-(2-methyl-3H-imidazo[4,5-b]pyridin-6-yl)quinazoline

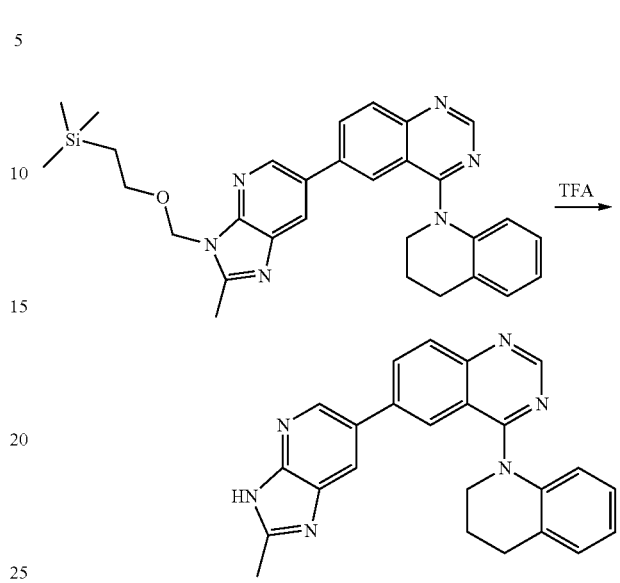

0.19 g of 4-(3,4-dihydro-2H-quinolin-1-yl)-6-[2-methyl-3-(2-trimethylsilanylethoxymethyl)-3H-imidazo[4,5-b]pyridin-6-yl]quinazoline and 200 µl of trifluoroacetic acid in 2 ml of dichloromethane are stirred at 25° C. in a flask until the reaction is complete (HPLC check, about 48 hours). The cooled reaction solution is evaporated to dryness in a rotary evaporator. The residue is purified by means of preparative HPLC (gradient water:acetonitrile 1-50% in 14 min.), giving 0.03 g of 4-(3,4-dihydro-2H-quinolin-1-yl)-6-(2-methyl-3H-imidazo-[4,5-b]pyridin-6-yl)quinazoline ("A5") as white solid (yield 23%, content 99%); MS-FAB (M+H$^+$)=393.1; R$_f$ (polar method): 1.41 min;

$^1$H NMR (500 MHz, DMSO-d$_6$) δ [ppm] 8.86 (s, 1H), 8.18-8.13 (m, 3H), 7.94 (d, J=8.6, 1H), 7.72 (d, J=22.6, 1H), 7.59 (s, 1H), 7.35 (d, J=7.0, 1H), 7.12 (t, J=7.6, 1H), 7.05 (t, J=7.4, 1H), 6.76 (d, J=7.6, 1H), 4.05 (t, J=6.5, 2H), 2.89 (t, J=6.5, 2H), 2.55 (s, 3H), 2.10-2.04 (m, 2H).

EXAMPLE 8

Preparation of 4-(3,4-dihydro-1H-isoquinolin-2-yl)-6-(2-methyl-3H-imidazo-[4,5-b]pyridin-6-yl)pyrido[3,2-d]pyrimidine ("A8")

8.1 Preparation of methyl 3-amino-6-[2-methyl-3-(2-trimethylsilanylethoxymethyl)-3H-imidazo[4,5-b]pyridin-6-yl]pyridine-2-carboxylate

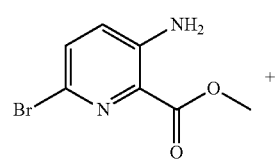

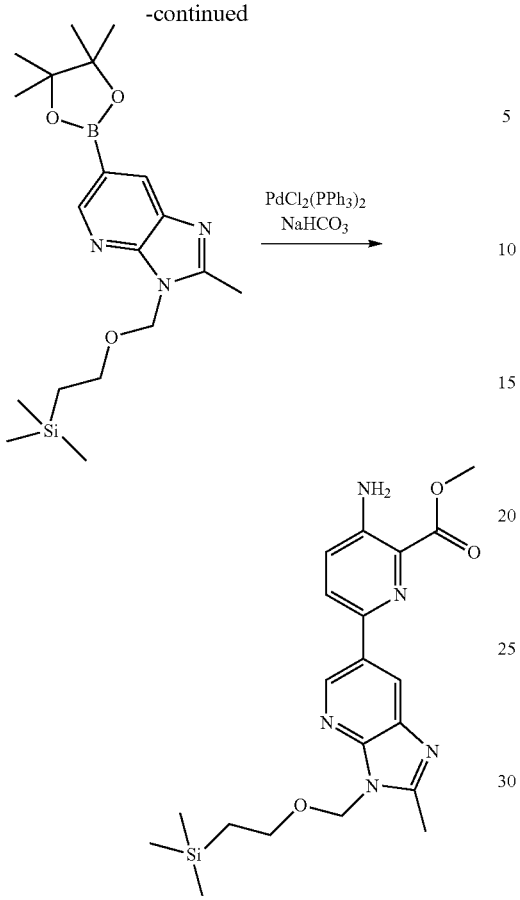

1.00 g of methyl 3-amino-6-bromopyridine-2-carboxylate, 2.00 g of 5-(4,4,5,5-tetramethyl-1,3,2-dioxaborolan-2-yl)-1-triisopropylsilanyl-1H-pyrrolo[2,3-b]pyridine, 1.00 g of sodium hydrogencarbonate and 0.30 g of $PdCl_2(PPh_3)_2$ in 20 ml of dioxane and 2 ml of water are heated at 90° C. under nitrogen in a flask until the reaction is complete (HPLC check, about 7 hours). The cooled reaction solution is diluted with EA and washed 3 times with water. The organic phase is dried over sodium sulfate and purified by means of column chromatography (gradient EA: methanol 0-20% in 30 min), giving 1.00 g of methyl 3-amino-6-[2-methyl-3-(2-trimethylsilanylethoxymethyl)-3H-imidazo-[4,5-b]pyridin-6-yl]pyridine-2-carboxylate as white solid (yield 60%, content 98%); MS-FAB (M+H$^+$)=414.2; R$_f$(polar method): 2.24 min.

8.2 Preparation of 6-[2-methyl-3-(2-trimethylsilanylethoxymethyl)-3H-imidazo[4,5-b]pyridin-6-yl]-3H-pyrido[3,2-d]pyrimidin-4-one

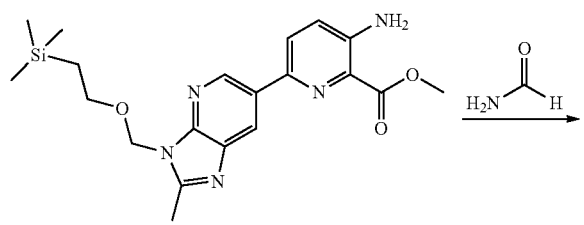

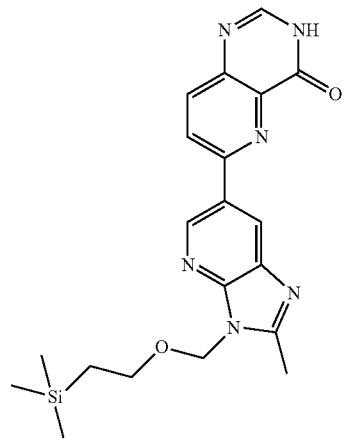

1.00 g of methyl 3-amino-6-[2-methyl-3-(2-trimethylsilanylethoxymethyl)-3H-imidazo[4,5-b]pyridin-6-yl]pyridine-2-carboxylate in 16 ml of formamide are heated at 130° C. under nitrogen in a flask until the reaction is complete (HPLC check, about 48 hours). The excess formamide is distilled off (120° C., 1 mbar). The residue is dissolved in dichloromethane, washed with water, dried and purified by means of column chromatography (gradient EA: methanol 0-50% in 15 min), giving 0.40 g of 6-[2-methyl-3-(2-trimethylsilanylethoxymethyl)-3H-imidazo[4,5-b]pyridin-6-yl]-3H-pyrido[3,2-d]pyrimidin-4-one as reddish solid (yield 36%, content 95%); MS-FAB (M+H$^+$)=409.1; R$_f$(polar method): 2.01 min.

8.3 Preparation of 4-(3,4-dihydro-1H-isoquinolin-2-yl)-6-[2-methyl-3-(2-trimethylsilanylethoxymethyl)-3H-imidazo[4,5-b]pyridin-6-yl]pyridine

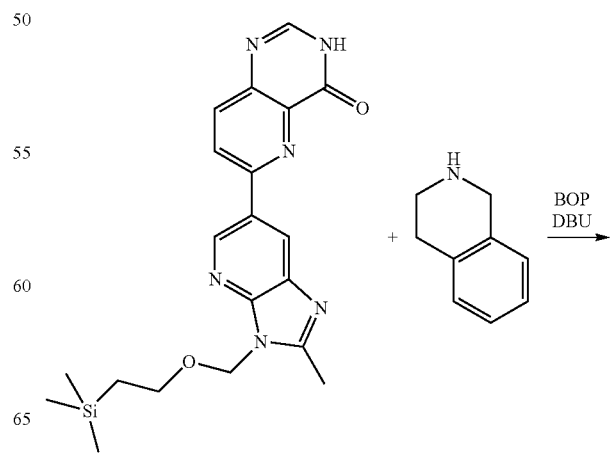

-continued

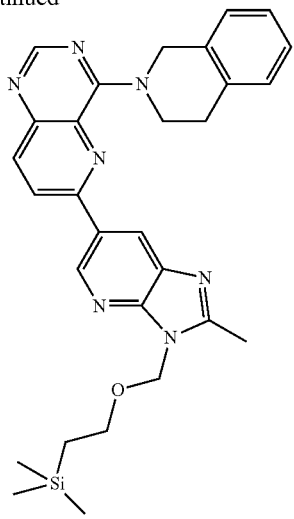

0.20 g of 6-[2-methyl-3-(2-trimethylsilanylethoxymethyl)-3H-imidazo[4,5-b]pyridin-6-yl]-3H-pyrido[3,2-d]pyrimidin-4-one and 89 μl of 1,2,3,4-tetrahydroisoquinoline are suspended in 6.00 ml of acetonitrile and 0.50 ml of dimethylformamide in a flask. 0.43 g of (benzotriazol-1-yloxy)tris-(dimethylamino)phosphonium hexafluorophosphate, 164 μl of 1,8-diazabicyclo[5.4.0]undec-7-ene are subsequently added, and the mixture is stirred at 25° C. under nitrogen until the reaction has proceeded to completion (HPLC check, about 4 hours). A precipitate precipitates out of the reaction solution. This is filtered off, rinsed with water and dried, giving 0.13 g of 4-(3,4-dihydro-1H-zisoquinolin-2-yl)-6-[2-methyl-3-(2-trimethylsilanylethoxymethyl)-3H-imidazo[4,5-b]pyridin-6-yl]pyridine as white solid (yield 50%, content 99%); MS-FAB (M+H⁺)=524.2; $R_f$(polar method): 2.53 min.

8.4 Preparation of 4-(3,4-dihydro-1H-isoquinolin-2-yl)-6-(2-methyl-3H-imidazo[4,5-b]pyridin-6-yl)pyrido[3,2-d]pyrimidine

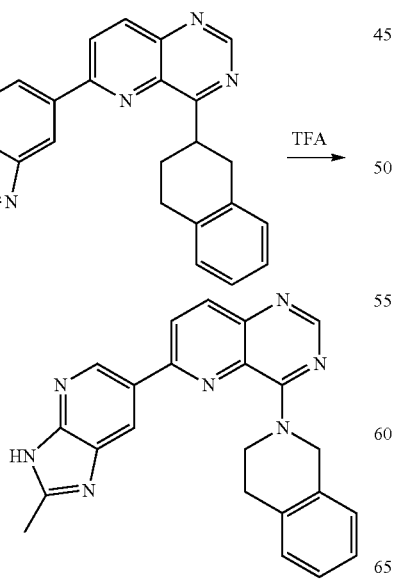

0.12 g of 4-(3,4-dihydro-1H-isoquinolin-2-yl)-6-[2-methyl-3-(2-trimethylsilanylethoxymethyl)-3H-imidazo[4,5-b]pyridin-6-yl]pyridine and 141 μl of trifluoroacetic acid in 1.50 ml of dichloromethane are stirred at 25° C. in a flask until the reaction is complete (HPLC check, about 24 hours). The cooled reaction solution is diluted with dichloromethane and washed with sodium hydrogencarbonate solution. The organic phase is dried over sodium sulfate, evaporated in a rotary evaporator, and the residue is suspended in acetonitrile. The solid is filtered off with suction and dried, giving 0.02 g of 4-(3,4-dihydro-1H-isoquinolin-2-yl)-6-(2-methyl-3H-imidazo[4,5-b]pyridin-6-yl)-pyrido[3,2-d]pyrimidine ("A8") as white solid (yield 24%, content 99%); MS-FAB (M+H⁺)=394.1; $R_f$(polar method): 1.47 min;

¹H NMR (400 MHz, DMSO-d₆) δ [ppm] 9.50 (dd, J=26.0, 1.7, 1H), 9.13-8.99 (m, 2H), 8.89 (d, J=8.9, 1H), 8.48 (d, J=8.9, 1H), 7.51-7.38 (m, 1H), 7.38-7.17 (m, 3H), 6.31 (s, 1H), 5.50 (s, 1H), 5.18 (t, J=5.7, 1H), 4.57 (t, J=5.8, 1H), 3.39 (t, J=5.7, 1H), 3.21 (t, J=5.6, 1H), 2.95 (d, J=3.8, 3H).

EXAMPLE 9

Preparation of 4-(6,7-dimethoxy-3,4-dihydro-1H-isoquinolin-2-yl)-6-(2-methyl-3H-imidazo[4,5-b]pyridin-6-yl)pyrido[3,2-d]pyrimidine ("A9")

9.1 Preparation of 4-(6,7-dimethoxy-3,4-dihydro-1H-isoquinolin-2-yl)-6-[2-methyl-3-(2-trimethylsilanylethoxymethyl)-3H-imidazo[4,5-b]pyridine

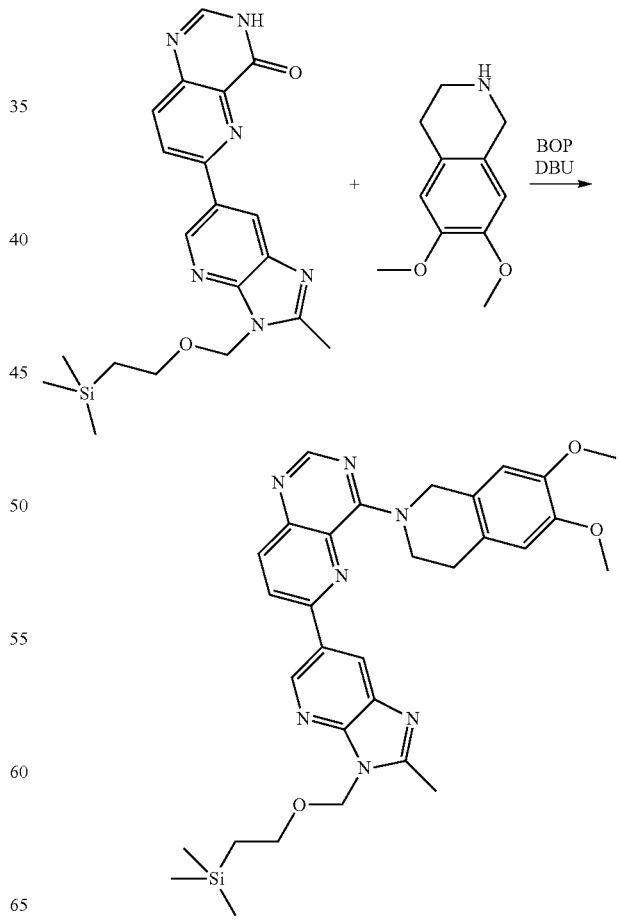

0.35 g of 6-[2-methyl-3-(2-trimethylsilanylethoxymethyl)-3H-imidazo[4,5-b]pyridin-6-yl]-3H-pyrido[3,2-d]pyrimidin-4-one and 0.18 g of 6,7-dimethoxy-1,2,3,4-tetrahydroisoquinoline are suspended in 5 ml of acetonitrile and 1 ml of dimethylformamide in a flask. 0.68 g of (benzotriazol-1-yloxy)tris-(dimethyl-amino)phosphonium hexafluorophosphate, 264 µl of 1,8-diazabicyclo[5.4.0]-undec-7-ene are subsequently added, and the mixture is stirred at 25° C. under nitrogen until the reaction has proceeded to completion (HPLC check, about 48 hours). A precipitate precipitates out of the reaction solution. This is filtered off and purified by means of column chromatography (gradient EA: methanol 0-40% in 20 min), giving 0.07 g of 4-(6,7-dimethoxy-3,4-dihydro-1H-isoquinolin-2-yl)-6-[2-methyl-3-(2-trimethylsilanylethoxymethyl)-3H-imidazo[4,5-b]pyridine as white solid (yield 15%, content 93%); MS-FAB (M+H$^+$)=584.2; R$_f$ (polar method): 2.26 min.

9.2 Preparation of 4-(6,7-dimethoxy-3,4-dihydro-1H-isoquinolin-2-yl)-6-(2-methyl-3H-imidazo[4,5-b]pyridin-6-yl)pyrido[3,2-d]pyrimidine

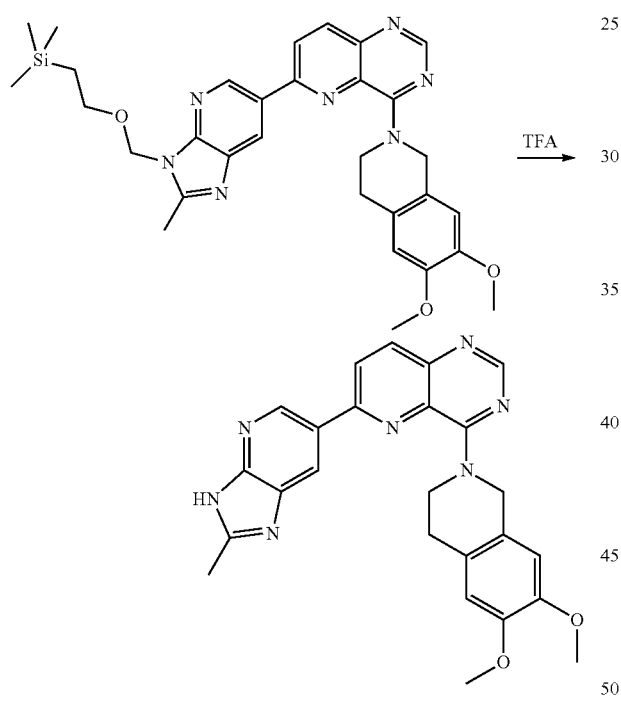

0.07 g of 4-(6,7-dimethoxy-3,4-dihydro-1H-isoquinolin-2-yl)-6-[2-methyl-3-(2-trimethylsilanylethoxymethyl)-3H-imidazo[4,5-b]pyridine and 141 µl of trifluoroacetic acid in 1 ml of dichloromethane are stirred at 25° C. in a flask until the reaction is complete (HPLC check, about 24 hours). The cooled reaction solution is evaporated to dryness in a rotary evaporator. The residue is purified by means of prep. HPLC (gradient water:acetonitrile 1-50% in 14 min.), giving 0.01 g of 4-(6,7-dimethoxy-3,4-dihydro-1H-isoquinolin-2-yl)-6-(2-methyl-3H-imidazo[4,5-b]pyridin-6-yl)pyrido-[3,2-d]pyrimidine ("A9") as white solid (yield 30%, content 99%); MS-FAB (M+H$^+$)=454.2 R$_f$ (polar method): 1.41 min;
$^1$H NMR (500 MHz, DMSO-d$_6$) δ [ppm] 9.37 (s, 1H), 8.90 (s, 1H), 8.86 (s, 1H), 8.73 (d, J=8.9, 1H), 8.41 (d, J=8.9, 1H), 6.90 (s, 1H), 6.86 (s, 1H), 3.77 (s, 6H), 3.17 (s, 2H), 2.88 (s, 3H), 1.21 (t, J=7.1, 2H).

EXAMPLE 10

Preparation of 4-(7-methoxy-3,4-dihydro-1H-isoquinolin-2-yl)-6-(2-methyl-3H-imidazo[4,5-b]pyridin-6-yl)quinazoline ("A11")

10.1 Preparation of 6-iodo-4-(7-methoxy-3,4-dihydro-1H-isoquinolin-2-yl)-quinazoline

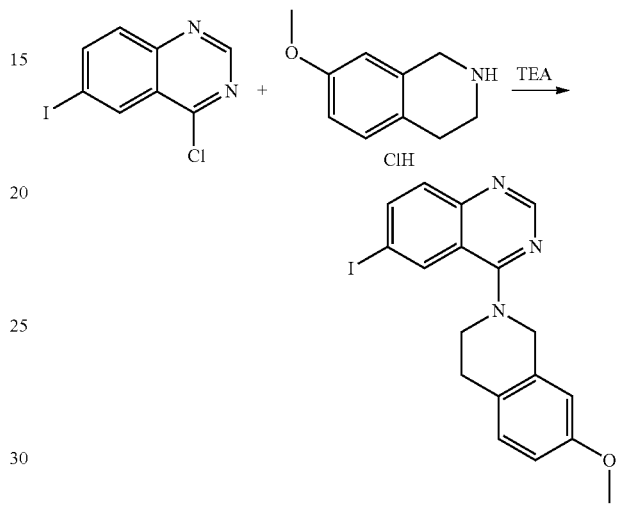

0.75 g of 4-chloro-6-iodoquinazoline, 0.58 g of 7-methoxy-1,2,3,4-tetrahydroisoquinoline and 0.64 ml of triethylamine in 5 ml of dioxane are heated at 80° C. in a flask until the quinazoline has reacted completely (HPLC check, about 2 hours). The cooled reaction solution is diluted with EA and washed 3 times with water. The organic phase is dried over sodium sulfate and purified by means of column chromatography (gradient heptane: EA 5-100% in 22 min.), giving 0.60 g of 6-iodo-4-(7-methoxy-3,4-dihydro-1H-isoquinolin-2-yl) quinazoline as yellowish solid (yield 57%, content 93%); MS-FAB (M+H$^+$)=418.0; R$_f$ (polar method): 1.87 min.

10.2 Preparation of 4-(7-methoxy-3,4-dihydro-1H-isoquinolin-2-yl)-6-[2-methyl-3-(2-trimethylsilanylethoxymethyl)-3H-imidazo]4,5-b]pyridin-6-yl]quinazoline

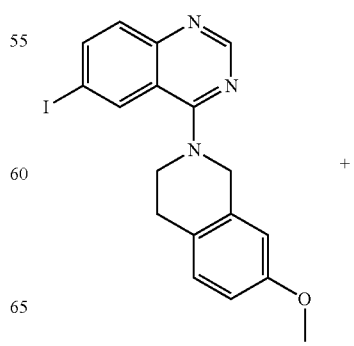

-continued

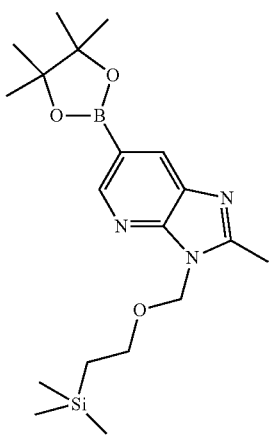

10.3 Preparation of 4-(7-methoxy-3,4-dihydro-1H-isoquinolin-2-yl)-6-(2-methyl-3H-imidazo[4,5-b]pyridin-6-yl)quinazoline

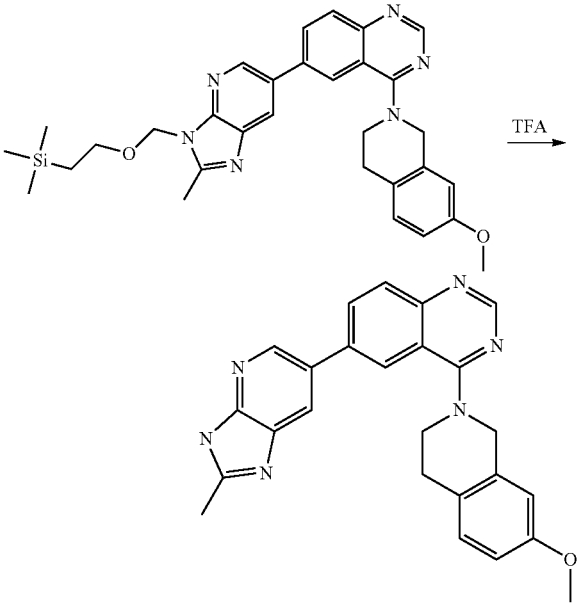

0.19 g of 4-(7-methoxy-3,4-dihydro-1H-isoquinolin-2-yl)-6-[2-methyl-3-(2-trimethylsilanylethoxymethyl)-3H-imidazo]4,5-b]pyridin-6-yl]quinazoline and 175 µl of trifluoroacetic acid in 2 ml of dichloromethane are stirred at 25° C. in a flask until the reaction is complete (HPLC check, about 72 hours). The cooled reaction solution is evaporated to dryness in a rotary evaporator. The residue is purified by means of preparative HPLC. (gradient water:acetonitrile 1-40% in 14 min.), giving 0.02 g of 4-(7-methoxy-3,4-dihydro-1H-isoquinolin-2-yl)-6-(2-methyl-3H-imidazo[4,5-b]pyridin-6-yl)quinazoline ("A11") as white solid (yield 21%, content 99%); MS-FAB (M+H$^+$)=423.1; R$_f$(polar method): 1.38 min;
$^1$H NMR (500 MHz, DMSO-d$_6$) δ [ppm] 9.12 (d, J=1.7, 1H), 8.94 (s, 1H), 8.73 (d, J=1.8, 1H), 8.68 (s, 1H), 8.48 (dd, J=8.8, 1.6, 1H), 8.05 (d, J=8.7.1H), 7.39 (s, 1H), 7.31 (d, J=6.1, 3H), 5.45 (s, 2H), 4.49 (s, 2H), 3.26 (q, J=7.6, 2H), 3.19 (t, J=5.3, 2H), 1.52 (t, J=7.6, 3H).

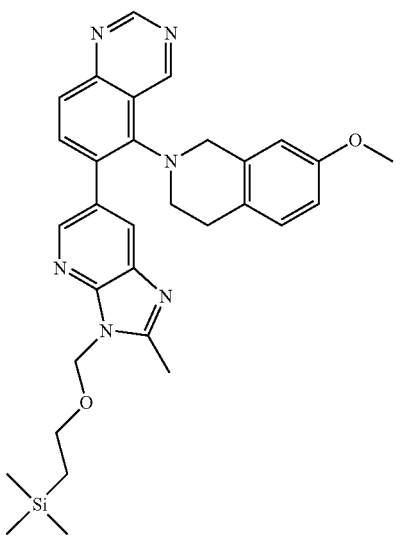

0.20 g of 6-iodo-4-(7-methoxy-3,4-dihydro-1H-isoquinolin-2-yl)quinazoline, 0.28 g of 5-(4,4,5,5-tetramethyl-1,3,2-dioxaborolan-2-yl)-1-triisopropylsilanyl-1H-pyrrolo[2,3-b]pyridine, 0.11 g of sodium hydrogencarbonate and 0.03 g of Pd(PPh$_3$)$_2$Cl$_2$ in 5.00 ml of dioxane and 0.50 ml of water are heated at 90° C. under nitrogen in a flask until the reaction is complete (HPLC check, about 5 hours). The cooled reaction solution is diluted with EA and washed 3 times with water. The organic phase is dried over sodium sulfate and purified by means of column chromatography (gradient EA: methanol 5-30% in 13 min), giving 0.20 g of 4-(7-methoxy-3,4-dihydro-1H-isoquinolin-2-yl)-6-[2-methyl-3-[(2-trimethylsilanylethoxymethyl)-3H-imidazo]4,5-b]pyridin-6-yl]quinazoline as white powder (yield 64%, content 79%); MS-FAB (M+H$^+$)=553.3; R$_f$(polar method): 2.14 min.

EXAMPLE 11

Preparation of 4-[6-(2-methyl-3H-imidazo[4,5-b]pyridin-6-yl)quinazolin-4-yl]-3,4-dihydro-2H-benzo-1,4-oxazine ("A12")

11.1 Preparation of 4-(6-iodoquinazolin-4-yl)-3,4-dihydro-2H-benzo-1,4-oxazine

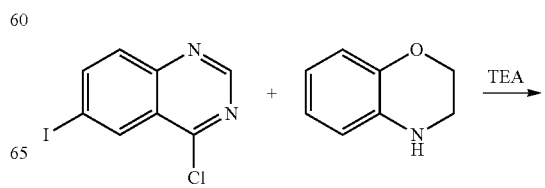

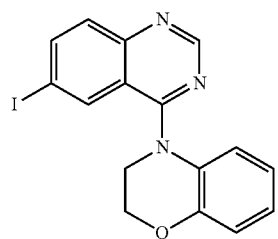

0.75 g of 4-chloro-6-iodoquinazoline, 0.39 g of 3,4-dihydro-2H-benzo-1,4-oxazine and 0.50 ml of triethylamine in 5 ml of dioxane are heated at 80° C. in a flask until the quinazoline has reacted completely (HPLC check, about 24 hours). The cooled reaction solution is evaporated to dryness. The residue is washed by stirring with EA and filtered off with suction, giving 0.35 g of 4-(6-iodoquinazolin-4-yl)-3,4-dihydro-2H-benzo-1,4-oxazine as yellowish solid (yield 40%, content 96%); MS-FAB (M+H$^+$)=390.0; R$_f$ (polar method): 2.36 min.

11.2 Preparation of 4-{6-[2-methyl-3-(2-trimethylsilanylethoxymethyl)-3H-imidazo[4,5-b]pyridin-6-yl]quinazolin-4-yl}-3,4-dihydro-2H-benzo[-1,4-oxazine

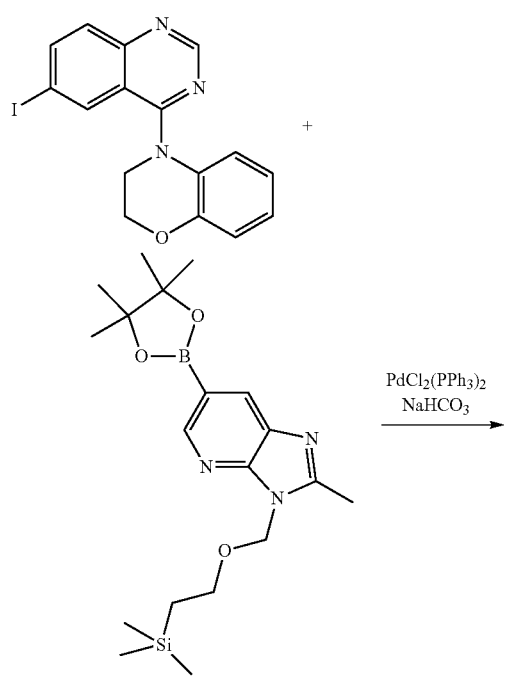

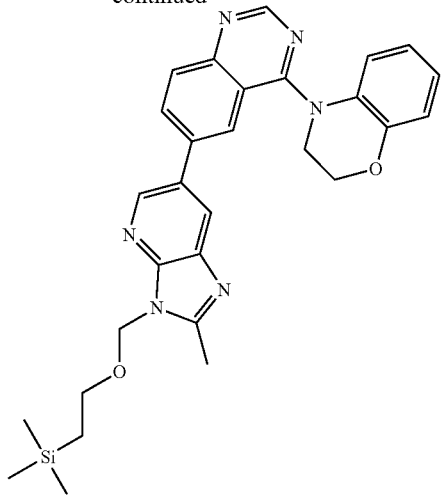

0.20 g of 4-(6-iodoquinazolin-4-yl)-3,4-dihydro-2H-benzo-1,4-oxazine, 0.32 g of 5-(4,4,5,5-tetramethyl-1,3,2-dioxaborolan-2-yl)-1-triisopropylsilanyl-1H-pyrrolo[2,3-b]pyridine, 0.12 g of sodium hydrogencarbonate and 0.03 g of Pd(PPh$_3$)$_2$Cl$_2$ in 5.00 ml of dioxane and 0.50 ml of water are heated at 90° C. under nitrogen in a flask until the reaction is complete (HPLC check, about 4 hours). The cooled reaction solution is diluted with EA and washed 3 times with water. The organic phase is dried over sodium sulfate and purified by means of column chromatography (gradient EA: methanol 0-20% in 15 min), giving 0.23 g of 4-{6-[2-methyl-3-(2-trimethylsilanylethoxymethyl)-3H-imidazo-[4,5-b]pyridin-6-yl]quinazolin-4-yl}-3,4-dihydro-2H-benzo-[1,4-oxazine as white powder (yield 78%, content 90%); MS-FAB (M+H$^+$)=525.2; R$_f$ (polar method): 2.51 min.

11.3 Preparation of 4-[6-(2-methyl-3H-imidazo[4,5-b]pyridin-6-yl)quinazolin-4-yl]-3,4-dihydro-2H-benzo-1,4-oxazine

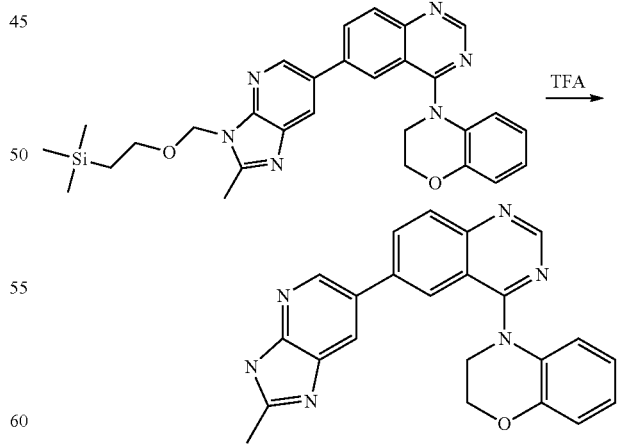

0.20 g of 4-{6-[2-methyl-3-(2-trimethylsilanylethoxymethyl)-3H-imidazo[4,5-b]-pyridin-6-yl]quinazolin-4-yl}-3,4-dihydro-2H-benzo-[1,4-oxazine and 211 µl of trifluoroacetic acid in 2 ml of dichloromethane are stirred at 25° C. in a flask until the reaction is complete (HPLC check, about 72 hours). The cooled reaction solution is evaporated to dryness in a rotary evaporator. The residue is purified by means of preparative HPLC (gradient water:acetonitrile 1-40% in 16 min.), giving 0.03 g of 4-[6-(2-methyl-3H-imidazo[4,5-b]pyridin-6-yl)quinazolin-4-yl]-3,4-dihydro-2H-benzo-1,4-oxazine ("A12") as white solid (yield 22%, content 100%); MS-FAB (M+H$^+$)=395.1; $R_f$(polar method): 1.43 min;

$^1$H NMR (500 MHz, DMSO-d$_6$) δ [ppm] 9.14 (s, 1H), 8.62 (d, J=1.9, 1H), 8.43 (dd, J=8.8, 1.9, 1H), 8.28 (d, J=1.9, 1H), 8.22 (d, J=1.6, 1H), 8.07 (d, J=8.8, 1H), 7.32 (dd, J=8.2, 1.2, 1H), 7.25 (ddd, J=8.5, 7.4, 1.4, 1H), 7.07 (dd, J=8.3, 1.3, 1H), 6.87-6.80 (m, 1H), 4.56 (s, 4H), 2.81 (s, 3H).

EXAMPLE 12

Preparation of 1-[6-(2-methyl-3H-imidazo[4,5-b]pyridin-6-yl)quinazolin-4-yl]-2,3-dihydro-1H-quinolin-4-one ("A13")

12.1 Preparation of 1-(6-iodoquinazolin-4-yl)-2,3,4a,8a-tetrahydro-1H-quinolin-4-one

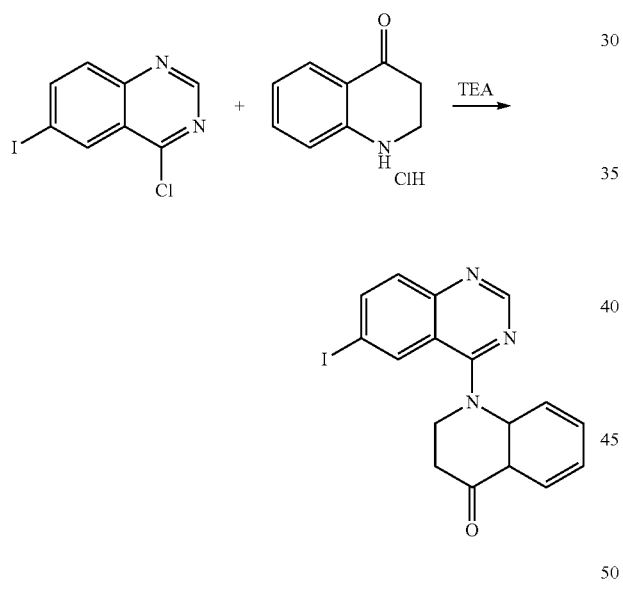

12.2 Preparation of 1-{6-[2-methyl-3-(2-trimethylsilanylethoxymethyl)-3H-imidazo[4,5-b]pyridin-6-yl]quinazolin-4-yl}-2,3-dihydro-1H-quinolin-4-one

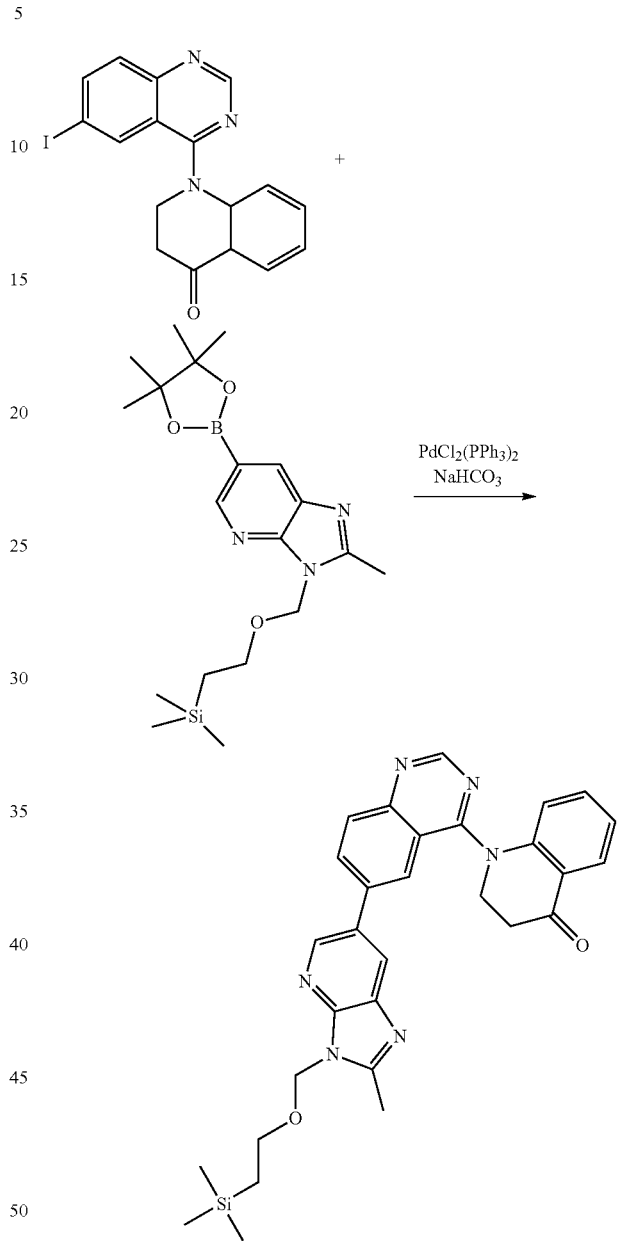

0.75 g of 4-chloro-6-iodoquinazoline, 0.51 g of 2,3,4a,8a-tetrahydro-1H-quinolin-4-one and 0.96 ml of triethylamine in 5 ml of dioxane are heated at 80° C. in a flask until the quinazoline has reacted completely (HPLC check, about 24 hours). The cooled reaction solution is diluted with EA and washed 3 times with water. The organic phase is dried over sodium sulfate and purified by means of column chromatography (gradient heptane: EA 5-100% in 16 min.), giving 0.40 g of 1-(6-iodoquinazolin-4-yl)-2,3,4a,8a-tetrahydro-1H-quinolin-4-one as yellowish solid (yield 40%, content 91%); MS-FAB (M+H$^+$)=402.0; $R_f$(polar method): 2.20 min.

0.25 g of 1-(6-iodoquinazolin-4-yl)-2,3,4a,8a-tetrahydro-1H-quinolin-4-one, 0.26 g of 5-(4,4,5,5-tetramethyl-1,3,2-dioxaborolan-2-yl)-1-triisopropylsilanyl-1H-pyrrolo[2,3-b]pyridine, 0.13 g of sodium hydrogencarbonate and 0.04 g of Pd(PPh$_3$)$_2$Cl$_2$ in 5.00 ml of dioxane and 0.50 ml of water are heated at 90° C. under nitrogen in a flask until the reaction is complete (HPLC check, about 4 hours). The cooled reaction solution is diluted with EA and washed 3 times with water. The organic phase is dried over sodium sulfate and purified by means of column chromatography (gradient EA: methanol 0-30% in 14 min), giving 0.25 g of 1-{6-[2-methyl-3-(2-trimethylsilanylethoxymethyl)-3H-imidazo-[4,5-b]pyridin-6-yl]quinazolin-4-yl}-2,3-dihydro-1H-quinolin-4-one as white powder (yield 73%, content 89%); MS-FAB (M+H$^+$)=237.2; $R_f$(polar method): 2.50 min.

12.3 Preparation of 1-[6-(2-methyl-3H-imidazo[4,5-b]pyridin-6-yl)quinazolin-4-yl]-2,3-dihydro-1H-quinolin-4-one

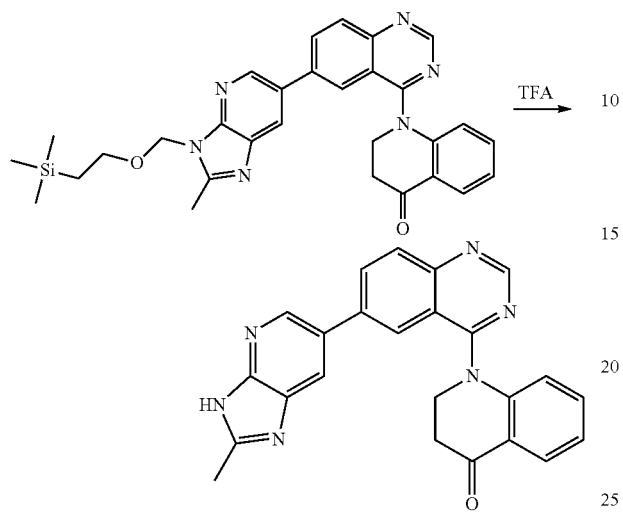

0.25 g of 1-{6-[2-methyl-3-(2-trimethylsilanylethoxymethyl)-3H-imidazo[4,5-b]-pyridin-6-yl]quinazolin-4-yl}-2,3-dihydro-1H-quinolin-4-one and 255 µl of trifluoroacetic acid in 2 ml of dichloromethane are stirred at 25° C. in a flask until the reaction is complete (HPLC check, about 72 hours). The cooled reaction solution is evaporated to dryness in a rotary evaporator. The residue is purified by means of preparative HPLC (gradient water:acetonitrile 1-50% in 16 min.), giving 0.04 g of 1-[6-(2-methyl-3H-imidazo[4,5-b]pyridin-6-yl)-quinazolin-4-yl]-2,3-dihydro-1H-quinolin-4-one ("A13") as white solid (yield 23%, content 99%); MS-FAB (M+H$^+$)=407.1; R$_f$ (polar method): 1.50 min;

$^1$H NMR (400 MHz, DMSO-d$_6$) δ [ppm] 9.34 (s, 1H), 8.55 (d, J=2.0, 1H), 8.51 (dd, J=8.8, 1.9, 1H), 8.22 (d, J=2.0, 1H), 8.18 (d, J=8.8, 1H), 8.16-8.09 (m, 1H), 8.00 (d, J=1.7, 1H), 7.56 (dd, J=6.7, 2.9, 2H), 7.48-7.40 (m, 1H), 4.91 (s, 2H), 3.12 (dd, J=13.2, 6.4, 2H), 2.88 (s, 3H).

EXAMPLE 13

Preparation of 4-(3,4-dihydro-1H-isoquinolin-2-yl)-6-(2-ethyl-3H-imidazo-[4,5-b]pyridin-6-yl)quinazoline ("A10")

13.1 Preparation of 6-bromo-2-ethyl-3H-imidazo[4,5-b]pyridine

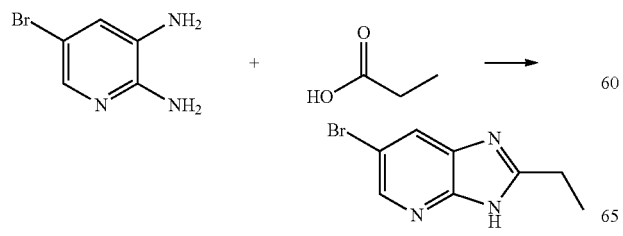

4 g of 5-bromopyridine-2,3-diamine in 40 ml of propionic acid is heated at 140° C. in a flask until the diamine has reacted completely (HPLC check, about 24 hours). The cooled reaction solution is evaporated to dryness. The residue is suspended in water, filtered off with suction and purified by means of column chromatography (gradient EA: methanol 5-40% in 30 min), giving 2.25 g of 6-bromo-2-ethyl-3H-imidazo[4,5-b]pyridine as yellowish solid (yield 45%, content 98%); MS-FAB (M+H$^+$)=228.0; R$_f$ (polar method): 1.27 min.

13.2 Preparation of 2-ethyl-6-(4,4,5,5-tetramethyl-1,3,2-dioxaborolan-2-yl)-3H-imidazo[4,5-b]pyridine

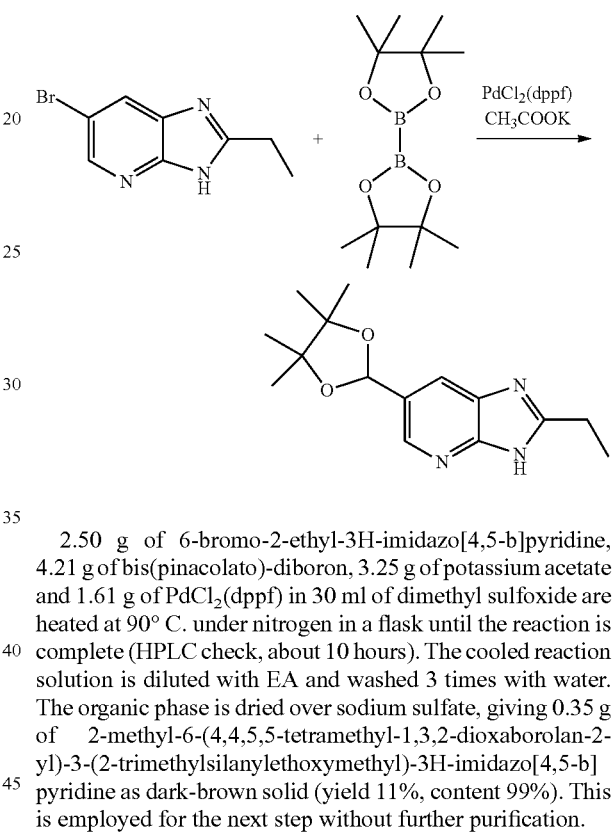

2.50 g of 6-bromo-2-ethyl-3H-imidazo[4,5-b]pyridine, 4.21 g of bis(pinacolato)-diboron, 3.25 g of potassium acetate and 1.61 g of PdCl$_2$(dppf) in 30 ml of dimethyl sulfoxide are heated at 90° C. under nitrogen in a flask until the reaction is complete (HPLC check, about 10 hours). The cooled reaction solution is diluted with EA and washed 3 times with water. The organic phase is dried over sodium sulfate, giving 0.35 g of 2-methyl-6-(4,4,5,5-tetramethyl-1,3,2-dioxaborolan-2-yl)-3-(2-trimethylsilanylethoxymethyl)-3H-imidazo[4,5-b]pyridine as dark-brown solid (yield 11%, content 99%). This is employed for the next step without further purification.

13.3 Preparation of 4-(3,4-dihydro-1H-isoquinolin-2-yl)-6-(2-ethyl-3H-imidazo[4,5-b]pyridin-6-yl)quinazoline

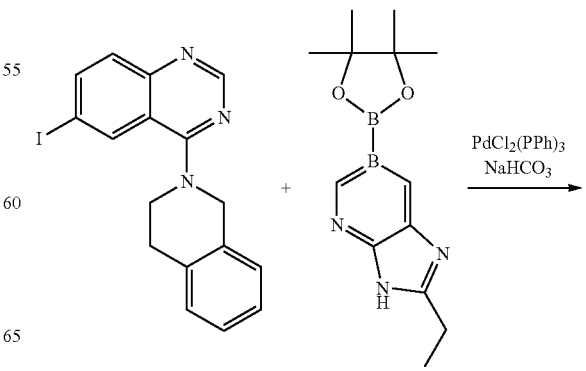

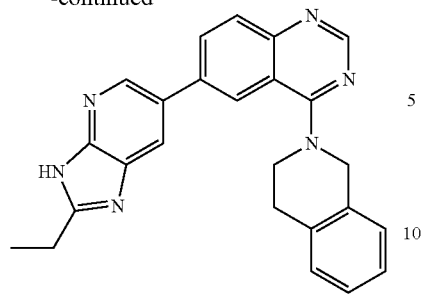

0.25 g of 4-(3,4-dihydro-1H-isoquinolin-2-yl)-6-iodoquinazoline, 0.35 g of 2-ethyl-6-(4,4,5,5-tetramethyl-1,3,2-dioxaborolan-2-yl)-3H-imidazo[4,5-b]pyridine, 0.52 g of sodium hydrogencarbonate and 0.29 g of Pd(PPh$_3$)$_2$Cl$_2$ in 17 ml of dioxane and 2 ml of water are heated at 90° C. under nitrogen in a flask until the reaction is complete (HPLC check, about 3 hours). The cooled reaction solution is diluted with EA and washed 3 times with water. The organic phase is dried over sodium sulfate and purified by means of column chromatography (gradient EA: methanol 0-45% in 16 min), giving 0.05 g of 4-(3,4-dihydro-1H-isoquinolin-2-yl)-6-(2-ethyl-3H-imidazo[4,5-b]pyridin-6-yl)quinazoline ("A10") as white powder (yield 92%, content 94%); MS-FAB (M+H$^+$)=407.2; R$_f$ (polar method): 1.40 min;

$^1$H NMR (500 MHz, DMSO-d$_6$) δ [ppm] 9.12 (d, J=1.7, 1H), 8.94 (s, 1H), 8.73 (d, J=1.8, 1H), 8.68 (s, 1H), 8.48 (dd, J=8.8, 1.6, 1H), 8.05 (d, J=8.7, 1H), 7.39 (s, 1H), 7.31 (d, J=6.1, 3H), 5.45 (s, 2H), 4.49 (s, 2H), 3.26 (q, J=7.6, 2H), 3.19 (t, J=5.3, 2H), 1.52 (t, J=7.6, 3H).

DNA-PK and PI3 Kinase Inhibition

TABLE 1

| Compound No. | DNA-PK IC50 | PI3K (cellular) IC50 |
|---|---|---|
| "A1" | A | B |
| "A2" | A | B |
| "A3" | A | B |
| "A4" | A | A |
| "A5" | A | B |
| "A6" | A | B |
| "A7" | A | |
| "A8" | A | A |
| "A9" | A | A |
| "A10" | A | A |
| "A11" | A | A |
| "A12" | A | B |
| "A13" | A | B |

IC$_{50}$:
1 nM-0.1 μM = A
0.1 μM-10 μM = B
>10 μM = C

The following examples relate to medicaments:

EXAMPLE A

Injection Vials

A solution of 100 g of an active compound of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active compound.

EXAMPLE B

Suppositories

A mixture of 20 g of an active compound of the formula I with 100 g of soya lecithin and 1400 g of cocoa butter is melted, poured into moulds and allowed to cool. Each suppository contains 20 mg of active compound.

EXAMPLE C

Solution

A solution is prepared from 1 g of an active compound of the formula I, 9.38 g of NaH$_2$PO$_4$.2H$_2$O, 28.48 g of Na$_2$HPO$_4$.12H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active compound of the formula I are mixed with 99.5 g of Vaseline under aseptic conditions.

EXAMPLE E

Tablets

A mixture of 1 kg of active compound of the formula I, 4 kg of lactose, 1.2 kg of potato starch, 0.2 kg of talc and 0.1 kg of magnesium stearate is pressed in a conventional manner to give tablets in such a way that each tablet contains 10 mg of active compound.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active compound of the formula I are introduced into hard gelatine capsules in a conventional manner in such a way that each capsule contains 20 mg of the active compound.

EXAMPLE H

Ampoules

A solution of 1 kg of active compound of the formula I in 60 l of bidistilled water is sterile filtered, transferred into ampoules, lyophilised under sterile conditions and sealed under sterile conditions. Each ampoule contains 10 mg of active compound.

The invention claimed is:
1. A compound of the formula I

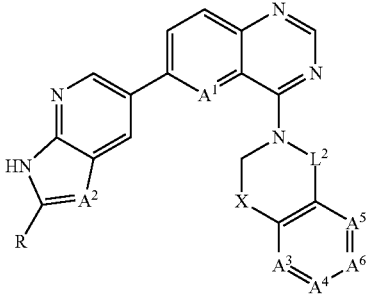

in which
A¹ denotes N or CR¹,
A² denotes N or CR²,
A³, A⁴,
A⁵, A⁶ each, independently of one another, denote N or CR³,
X is absent or denotes alkylene having 1 or 2 C atoms, in which H atoms may be replaced by OH, F and/or Cl, and/or in which one CH₂ group may be replaced by O, N, NH, NA', CO, S, SO, SO₂, OCO, NHCONH, NHCO, NHSO₂, COO, CONH and/or CH=CH groups,
L² is absent or denotes alkylene having 1 or 2 C atoms, in which H atoms may be replaced by OH, F and/or Cl, and/or in which one CH₂ group may be replaced by O, N, NH, NA', CO, S, SO, SO₂, OCO, NHCONH, NHCO, NHSO₂, COO, CONH and/or CH=CH groups,
with the proviso that X and L² cannot be absent simultaneously,
R denotes H or unbranched or branched alkyl having 1-10 C atoms, in which 1-7H atoms may be replaced by F and/or Cl and/or in which one or two non-adjacent CH and/or CH₂ groups may be replaced by O, N, NH, NA', CO, S, SO, SO₂, OCO, NHCONH, NHCO, NHSO₂, COO, CONH and/or CH=CH groups,
or
cyclic alkyl having 3-7 C atoms,
R¹ denotes H or unbranched or branched alkyl having 1-10 C atoms, in which 1-7H atoms may be replaced by F and/or Cl and/or in which one or two non-adjacent CH and/or CH₂ groups may be replaced by O, N, NH, NA', CO, S, SO, SO₂, OCO, NHCONH, NHCO, NHSO₂, COO, CONH and/or CH=CH groups,
or
cyclic alkyl having 3-7 C atoms,
R² denotes H or unbranched or branched alkyl having 1-10 C atoms, in which 1-7H atoms may be replaced by F and/or Cl and/or in which one or two non-adjacent CH and/or CH₂ groups may be replaced by O, N, NH, NA', CO, S, SO, SO₂, OCO, NHCONH, NHCO, NHSO₂, COO, CONH and/or CH=CH groups,
or
cyclic alkyl having 3-7 C atoms,
R³ denotes H or unbranched or branched alkyl having 1-10 C atoms, in which 1-7H atoms may be replaced by F and/or Cl and/or in which one or two non-adjacent CH and/or CH₂ groups may be replaced by O, N, NH, NA', CO, S, SO, SO₂, OCO, NHCONH, NHCO, NHSO₂, COO, CONH and/or CH=CH groups,
or
cyclic alkyl having 3-7 C atoms,
A' in each case, independently of one another, denotes unbranched or branched alkyl having 1-10 C atoms,
in which 1-7H atoms may be replaced by F and/or Cl,
and/or in which one or two non-adjacent CH and/or CH₂ groups may be replaced by O, N, NH, NA, S, SO, SO₂ and/or CH=CH groups,
or
cyclic alkyl having 3-7 C atoms,
A denotes alkyl having 1, 2, 3 or 4 C atoms,
or a pharmaceutically usable salt tautomer or stereoisomer thereof, including mixtures thereof in all ratios.

2. A compound according to claim 1 in which
A³, A⁴, A⁵, A⁶ denote CR³,
or a pharmaceutically usable salt, tautomer or stereoisomer thereof, including mixtures thereof in all ratios.

3. A compound according to claim 1 in which
X is absent or denotes alkylene having 1 or 2 C atoms, and in which one CH₂ group may be replaced by O, NH, CO or SO₂,
or a pharmaceutically usable salt, tautomer or stereoisomer thereof, including mixtures thereof in all ratios.

4. A compound according to claim 1 in which
L² is absent or alkylene having 1 or 2 C atoms,
or a pharmaceutically usable salt, tautomer or stereoisomer thereof, including mixtures thereof in all ratios.

5. A compound according to claim 1 in which
R denotes H or unbranched or branched alkyl having 1-4 C atoms,
or a pharmaceutically usable salt, tautomer or stereoisomer thereof, including mixtures thereof in all ratios.

6. A compound according to claim 1 in which
R¹ denotes H,
or a pharmaceutically usable salt, tautomer or stereoisomer thereof, including mixtures thereof in all ratios.

7. A compound according to claim 1 in which
R² denotes H,
or a pharmaceutically usable salt, tautomer or stereoisomer thereof, including mixtures thereof in all ratios.

8. A compound according to claim 1 in which
R³ denotes H or unbranched or branched alkyl having 1-4 C atoms and in which one CH₂ group may be replaced by O,
or a pharmaceutically usable salt, tautomer or stereoisomer thereof, including mixtures thereof in all ratios.

9. A compound according to claim 1 in which
A¹ denotes N or CR¹,
A² denotes N or CR²,
A³, A⁴, A⁵, A⁶ denote CR³,
X is absent or denotes alkylene having 1 or 2 C atoms, and in which one CH₂ group may be replaced by O, NH, CO or SO₂,
L² is absent or denotes alkylene having 1 or 2 C atoms,
R denotes H or unbranched or branched alkyl having 1-4 C atoms,
R¹ denotes H,
R² denotes H,
R³ denotes H or unbranched or branched alkyl having 1-4 C atoms and in which one CH₂ group may be replaced by O,
or a pharmaceutically usable salt, tautomer or stereoisomer thereof, including mixtures thereof in all ratios.

10. A compound according to claim 1, selected from the following compounds:

| Compound No. | Name |
|---|---|
| "A1" | 4-(2,3-Dihydroindol-1-yl)-6-(1H-pyrrolo[2,3-b]pyridin-5-yl)quinazoline |
| "A2" | 4-(1,3-Dihydroisoindol-2-yl)-6-(1H-pyrrolo[2,3-b]-pyridin-5-yl)quinazoline |
| "A3" | 4-(3,4-Dihydro-2H-quinolin-1-yl)-6-(1H-pyrrolo[2,3-b]-pyridin-5-yl)quinazoline |
| "A4" | 4-(3,4-Dihydro-1H-isoquinolin-2-yl)-6-(2-methyl-3H-imidazo[4,5-b]pyridin-6-yl)quinazoline |
| "A5" | 4-(3,4-Dihydro-2H-quinolin-1-yl)-6-(2-methyl-3H-imidazo[4,5-b]pyridin-6-yl)quinazoline |
| "A6" | 4-(3,4-Dihydro-1H-isoquinolin-2-yl)-6-(1H-pyrrolo-[2,3-b]pyridin-5-yl)pyrido[3,2-d]pyrimidine |
| "A7" | 4-(6,7-Dimethoxy-3,4-dihydro-1H-isoquinolin-2-yl)-6-(1H-pyrrolo[2,3-b]pyridin-5-yl)pyrido[3,2-d]pyrimidine |
| "A8" | 4-(3,4-Dihydro-1H-isoquinolin-2-yl)-6-(2-methyl-3H-imidazo[4,5-b]pyridin-6-yl)pyrido[3,2-d]pyrimidine |
| "A9" | 4-(6,7-Dimethoxy-3,4-dihydro-1H-isoquinolin-2-yl)-6-(2-methyl-3H-imidazo[4,5-b]pyridin-6-yl)pyrido[3,2-d]pyrimidine |
| "A10" | 4-(3,4-Dihydro-1H-isoquinolin-2-yl)-6-(2-ethyl-3H-imidazo[4,5-b]pyridin-6-yl)quinazoline |
| "A11" | 4-(7-Methoxy-3,4-dihydro-1H-isoquinolin-2-yl)-6-(2-methyl-3H-imidazo[4,5-b]pyridin-6-yl)quinazoline |
| "A12" | 4-[6-(2-Methyl-3H-imidazo[4,5-b]pyridin-6-yl)-quinazolin-4-yl]-3,4-dihydro-2H-benzo-1,4-oxazine |
| "A13" | 1-[6-(2-Methyl-3H-imidazo[4,5-b]pyridin-6-yl)-quinazolin-4-yl]-2,3-dihydro-1H-quinolin-4-one | or a pharmaceutically usable salt, tautomer or stereoisomer thereof, including mixtures thereof in all ratios.

11. A process for the preparation of a compound of the formula I according to claim 1 or a pharmaceutically usable salt, tautomer or stereoisomer thereof, comprising:
a) reacting a compound of the formula II

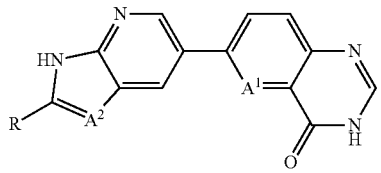

II in which R, $A^1$ and $A^2$ have the meanings indicated in claim 1,
with a compound of the formula III

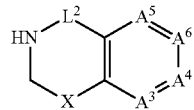

III in which X, $L^2$, $A^3$, $A^4$, $A^5$ and $A^6$ have the meanings indicated in claim 1,
or
b) reacting a compound of the formula IV

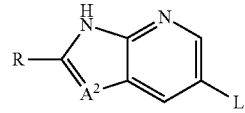

IV in which R and $A^2$ have the meanings indicated in claim 1 and L denotes a boronic acid or boronic acid ester radical,
with a compound of the formula V

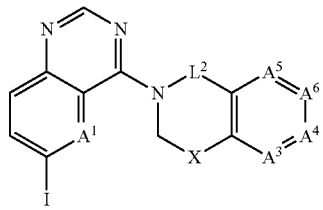

V in which X, $L^2$, $A^1$, $A^3$, $A^4$, $A^5$ and $A^6$ have the meanings indicated in claim 1,
and/or
c) converting a base or acid of the formula I into one of its salts.

12. A medicament composition comprising at least one compound of the formula I according to claim 1 or a pharmaceutically usable salt tautomer or stereoisomer thereof, including mixtures thereof in all ratios, and optionally excipients and/or adjuvants.

13. A kit comprising separate packs of
(a) an effective amount of a compound of the formula I according to claim 1, or a pharmaceutically usable salt, tautomer or stereoisomer thereof in all ratios, and
(b) an effective amount of a further medicament active compound.

14. A method for effecting DNA-PK and PI3 kinase inhibition in a patient, comprising administering a compound of formula I of claim 1 or a pharmaceutically usable salt, tautomer or stereoisomer thereof in all ratios.

15. A method for effecting PI3 kinase inhibition in a patient, comprising administering a compound of formula I of claim 1 or a pharmaceutically usable salt, tautomer or stereoisomer thereof in all ratios.

\* \* \* \* \*

UNITED STATES PATENT AND TRADEMARK OFFICE
CERTIFICATE OF CORRECTION

| | | |
|---|---|---|
| PATENT NO. | : 9,006,255 B2 | Page 1 of 1 |
| APPLICATION NO. | : 13/881531 | |
| DATED | : April 14, 2015 | |
| INVENTOR(S) | : Klein | |

It is certified that error appears in the above-identified patent and that said Letters Patent is hereby corrected as shown below:

In the Claims,

Column 72, line 26 reads "$L^2$ is absent or alkylene having 1 or 2 C atoms," should read -- $L^2$ is absent or denotes alkylene having 1 or 2 C atoms, --

Signed and Sealed this
Eleventh Day of August, 2015

Michelle K. Lee
*Director of the United States Patent and Trademark Office*